United States Patent
Ohtsuka et al.

(10) Patent No.: US 7,102,754 B2
(45) Date of Patent: *Sep. 5, 2006

(54) MEASURING METHOD AND APPARATUS USING ATTENUATION IN TOTAL INTERNAL REFLECTION

(75) Inventors: Hisashi Ohtsuka, Kaisei-machi (JP); Hitoshi Shimizu, Kaisei-machi (JP); Toshihito Kimura, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 56 days.

This patent is subject to a terminal disclaimer.

(21) Appl. No.: 10/932,270

(22) Filed: Sep. 2, 2004

(65) Prior Publication Data

US 2005/0030543 A1  Feb. 10, 2005

Related U.S. Application Data

(63) Continuation of application No. 10/273,270, filed on Oct. 18, 2002, now Pat. No. 6,791,691.

(30) Foreign Application Priority Data

Oct. 19, 2001 (JP) ............................. 2001-322406
Mar. 26, 2002 (JP) ............................. 2002-086421

(51) Int. Cl.
*G01N 21/55* (2006.01)
(52) U.S. Cl. ....................................... 356/445; 356/448
(58) Field of Classification Search ...................... None
See application file for complete search history.

(56) References Cited

U.S. PATENT DOCUMENTS

| 5,313,264 A | 5/1994 | Ivarsson et al. |
| 5,485,277 A | 1/1996 | Foster |
| 5,991,048 A | 11/1999 | Karlson et al. |
| 6,432,364 B1 | 8/2002 | Negami et al. |
| 6,570,657 B1 | 5/2003 | Hoppe et al. |
| 6,791,691 B1 * | 9/2004 | Ohtsuka et al. ............. 356/445 |
| 2002/0080358 A1 | 6/2002 | Shimizu |

FOREIGN PATENT DOCUMENTS

| EP | 1 186 881 A1 | 3/2002 |
| JP | 4-501462 | 3/1992 |
| JP | 6-167443 | 6/1994 |
| JP | 11-326194 | 11/1999 |
| JP | 2000-321280 A | 11/2000 |
| JP | 2001-330560 | 11/2001 |
| JP | 2002-525631 A | 8/2002 |
| WO | WO 00/19203 | 4/2000 |

OTHER PUBLICATIONS

Takayuki Okamoto; Surface Refracto-Sensor using Evanescent Waves: Principles and Instrumentations; Spectral Research; vol. 47. No. 1; Dec. 8, 1998.

* cited by examiner

*Primary Examiner*—Michael P. Stafira
(74) *Attorney, Agent, or Firm*—Sughrue Mion, PLLC

(57) ABSTRACT

A state of attenuation in total internal reflection is detected by the use of a measuring apparatus having a measuring unit and a reference unit and a measuring system which corrects result of detection by the measuring unit on the basis of result of detection by the reference unit and measures the change of a state of attenuation in total internal reflection on the basis of the corrected result of detection by the measuring unit. The difference in sensitivity between the measuring unit and the reference unit is detected before initiating the measurement of the change of a state of attenuation in total internal reflection, and result of measurement by the measuring system is calibrated on the basis of the difference in sensitivity between the measuring unit and the reference unit.

12 Claims, 16 Drawing Sheets

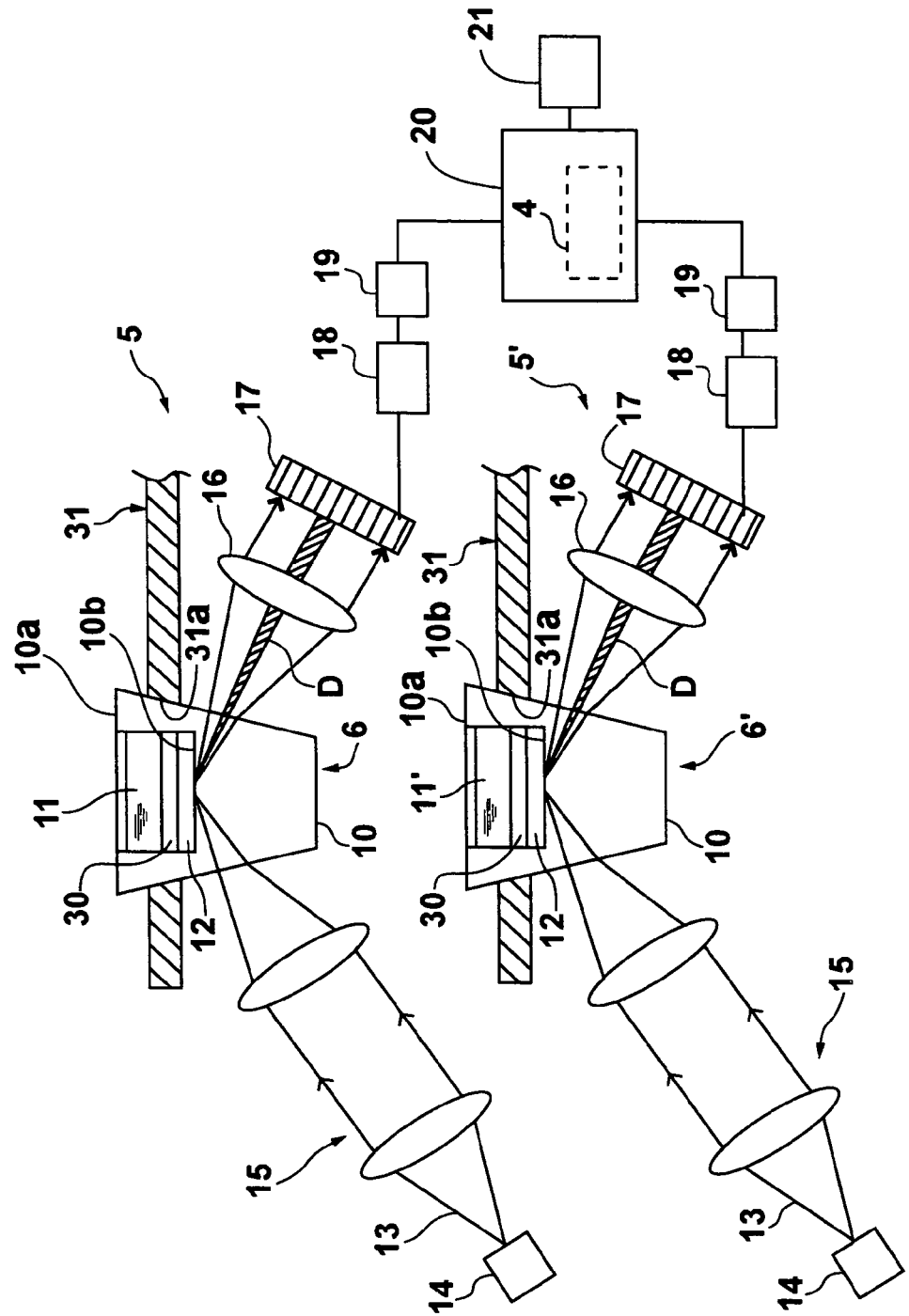

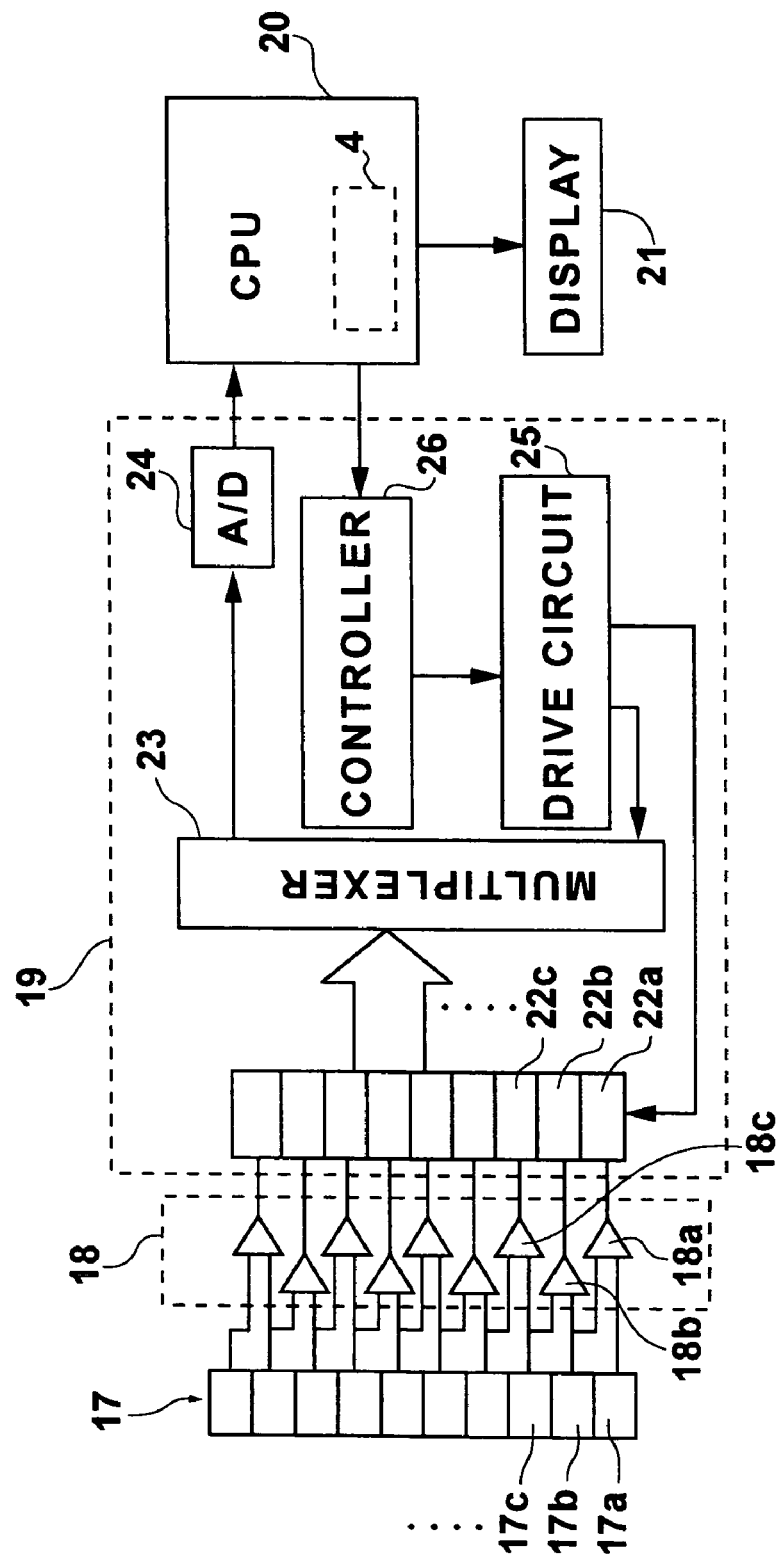

MEASURING METHOD AND APPARATUS USING ATTENUATION IN TOTAL INTERNAL REFLECTION

This is a continuation of application Ser. No. 10/273,270 filed Oct. 18, 2002, now U.S. Pat. No. 6,791,691 the specification of which is incorporated by reference.

BACKGROUND OF THE INVENTION

1. Field of the Invention

This invention relates to a measuring method and apparatus using attenuation in total internal reflection such as a surface plasmon sensor for analyzing a sample on the basis of generation of surface plasmon.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block to impinge upon the interface of the dielectric block and the metal film at various angles of incidence so that total internal reflection conditions are satisfied at the interface, and a photodetector means which detects the intensity of the light beam reflected in total internal reflection at the interface and detects a state of surface plasmon resonance, i.e., a state of attenuation in total internal reflection.

In order to obtain various angles of incidence of the light beam to the interface, a relatively thin incident light beam may be caused to impinge upon the interface while deflecting the incident light beam or a relatively thick incident light beam may be caused to impinge upon the interface in the form of convergent light or divergent light so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon resonance sensor, when a light beam impinges upon the interface at a particular angle of incidence θsp not smaller than the angle of, total internal reflection, evanescent waves having an electric field distribution in the sample in contact with the metal film are generated and surface plasmon is excited in the interface between the metal film and the sample. When the wave number vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector. The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, ω represents the angular frequency of the surface plasmon, c represents the speed of light in a vacuum, and $\in_m$ and $\in_s$ respectively represent the dielectric constants of the metal and the sample.

A property related to the dielectric constant $\in_s$ (refractive index) of the sample can be detected by detecting the angle of incidence θsp at which the intensity of light reflected in total internal reflection from the interface of the prism and the metal film sharply drops (this angel θsp will be referred to as "the attenuation angle θsp", hereinbelow).

In such a surface plasmon sensor, it has been proposed, in order to measure the attenuation angle θsp accurately with a wide dynamic range, to use a photodetector in the form of an array of a plurality of photodetector elements arranged in a predetermined direction so that light beam components reflected at different angles at the interface impinge upon different photodetector elements as disclosed in Japanese Unexamined Patent Publication No. 11 (1999)-326194.

In this case, the output signals output from the photodetector elements are generally differentiated in the direction in which the photodetector elements are arranged, and the refractive-index-related property of the material to be measured is generally obtained on the basis of the differentials.

As a similar apparatus utilizing the phenomenon of attenuation in total internal reflection (ATR), there has been known a leaky mode sensor described in, for instance, "Spectral Research" Vol.47, No.1 (1998), pp21 to 23 & pp26 and 27. The leaky mode sensor basically comprises a dielectric block shaped, for instance, like a prism, a clad layer which is formed on one face of the dielectric block, an optical waveguide layer which is formed on the clad layer and is brought into contact with a sample liquid, a light source emitting a light beam, an optical system which causes the light beam to enter the dielectric block to impinge upon the interface of the dielectric block and the metal film at various angles of incidence so that total internal reflection conditions are satisfied at the interface, and a photodetector means which detects the intensity of the light beam reflected in total internal reflection at the interface and detects a state of waveguide mode excitation, i.e., a state of attenuation in total internal reflection (ATR).

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence at which the attenuation in total internal reflection occurs.

Also in such a leaky mode sensor, a photodetector in the form of an array of a plurality of photodetector elements can be used to detect the position of the dark line generated due to the attenuation in total internal reflection, and at the same time differentiation of the output signals output from the photodetector elements is often applied.

The surface plasmon sensor and the leaky mode sensor are sometimes used in random screening for finding a specific material combined with a predetermined sensing material in the field of pharmacy. In this case, a sensing material is fixed on the film layer (the metal film in the case of the surface plasmon sensor and the clad layer and the optical waveguide layer in the case of the leaky mode sensor), and a sample liquid containing a material to be analyzed is spotted on the sensing material. Then the attenuation angle $\theta sp$ is repeatedly measured each time a predetermined time lapses.

When the sample material (the material to be analyzed in the sample liquid) is combined with the sensing material, the refractive index of the sensing material changes with time due to combination with the sample material. Accordingly, by measuring the attenuation angle $\theta sp$, at which attenuation in total internal reflection takes place, for every predetermined time, thereby detecting whether the attenuation angle $\theta sp$ changes (to know the state of combination of the sample material with the sensing material), it is possible to know whether the sample material is a specific material to be combined with the sensing material. As combinations of such a specific material and a sensing material, there have been known combinations of an antigen and an antibody and of an antibody and another antibody. For example, rabbit antihuman IgG antibody is fixed on the surface of the film layer as the sensing material with human IgG antibody employed as the specific material.

In order to detect the state of combination of the sample material with the sensing material, the total reflection attenuation angle $\theta sp$ (the angle of incidence $\theta sp$ at which attenuation in total internal reflection takes place) itself need not necessarily be detected. For example, the amount of change in the total reflection attenuation angle $\theta sp$ after the sample liquid is spotted onto the sensing material is measured and the state of combination of the sample material with the sensing material may be measured on the basis of the amount of change of the total reflection attenuation angle $\theta sp$. When a photodetector in the form of an array of a plurality of photodetector elements and differentiation of the output signals output from the photodetector elements are employed, the state of combination of the sample material with the sensing material can be measured on the basis of the amount of change of the differentiation of the output signals. (See our Japanese Patent Application 2000-398309.)

In the practical apparatuses utilizing the phenomenon of attenuation in total internal reflection such as a surface plasmon sensor or a leaky mode sensor, the amount of change of the total reflection attenuation angle $\theta sp$ is measured by spotting a sample liquid comprising solvent and a sample material onto a film layer formed on the bottom of a measuring chip in the form of a cup or dish.

When a sample liquid is spotted on a measuring chip and a sample material in the sample liquid is combined with the sensing material, the refractive index of the sensing material changes and the attenuation angle $\theta sp$ changes. However, strictly speaking, the change of the attenuation angle $\theta sp$ does not solely depend upon the state of combination of the sample material with the sensing material but also depends upon action between the sensing material and the solvent of the sample liquid and difference in sensitivity among measuring apparatuses.

That is, even when a false sample liquid which solely consists of solvent and includes no sample material is supplied to a sensing material, the attenuation angle $\theta sp$ slightly changes as shown by the solid line in FIG. 4. The change of the attenuation angle $\theta sp$ produces a measuring error. In order to avoid production of this measuring error, we, this applicant has proposed, in our Japanese Patent Application 2001-049681, a method of judging whether a sensing material is combined with a sample material, in which a corrected attenuation angle change is obtained by subtracting the change of the attenuation angle $\theta sp$ in a reference chip supplied with a false sample liquid from the change of the attenuation angle $\theta sp$ in a measuring chip supplied with a real sample liquid and whether the sensing material is combined with a sample material in the sample liquid is judged on the basis of the corrected attenuation angle change. In accordance with the method, since the corrected attenuation angle change becomes substantially 0 when the sensing material is not combined with the sample material, whether the sensing material is combined with a sample material in the sample liquid can be easily judged.

However, this method is disadvantageous in that since the corrected attenuation angle change does not become completely 0 even if the sensing material is not combined with the sample material, this method is not effective when the sample material is small in molecular weight though effective when the sample material is large in molecular weight.

The attenuation angle change in a measuring chip supplied with a false sample liquid as measured by these inventors is as shown by the solid line in FIG. 4, whereas the attenuation angle change in a reference chip supplied with the same false sample liquid as measured by these inventors is as shown by the broken line in FIG. 4. The corrected attenuation angle change in this case is as shown by the chained line in FIG. 4. Since the sensing material is combined with the sample material in neither cases, the corrected attenuation angle should be 0. However the attenuation angle change after one hour shown by the chained line shows a value of 900 in terms of molecular weight. That is, the corrected attenuation angle, which should be 0, is too large, which deteriorates the measuring accuracy.

A reason why there is produced a difference between the attenuation angle change in a reference chip and that in a measuring chip supplied with the same false sample liquid is, for instance, the difference in thickness of the metal films between the measuring chip and the reference chip. Another reason may be a difference in sensitivity between the photodetector means of the measuring unit and that of the reference unit.

Further, this applicant has disclosed a measuring apparatus utilizing the phenomenon of attenuation in total internal reflection in which a plurality of measuring chips are placed on, for instance, a turn table and are measured in sequence, thereby shortening the time required to measure a lot of samples. (Japanese Unexamined Patent Publication No. 2001-330560)

Further, this applicant has disclosed a measuring apparatus utilizing the phenomenon of attenuation in total internal reflection in which measuring chips each having a plurality of sample liquid holding portions are used so that measurement on a plurality of samples can be done at one time without moving the measuring chips. (Japanese Patent Application 2001-397411)

SUMMARY OF THE INVENTION

In view of the foregoing observations and description, the primary object of the present invention is to provide a measuring method and apparatus using attenuation in total internal reflection which can suppress the difference in sensitivity between the photodetector means of the measuring unit and that of the reference unit and can more accurately detect the state of attenuation in total internal reflection.

Another object of the present invention is to provide a measuring method and apparatus which can suppress the difference in sensitivity among measuring apparatuses and can more accurately analyze the sample.

In accordance with a first aspect of the present invention, there is provided a measuring method for detecting a state of attenuation in total internal reflection by the use of a measuring apparatus comprising a measuring unit comprising a first light source emitting a first light beam; a measuring chip consisting of a first dielectric block transparent to the first light beam, a first film layer formed on one face of the first dielectric block and a first sample liquid holding system which holds a sample liquid on the surface of the first film layer, the sample liquid comprising solvent and a sample; a sensing material which can be combined with a specific material in the sample liquid and is disposed on the first film layer; a first optical system which causes the first light beam to enter the first dielectric block to impinge upon the interface of the first dielectric block and the first film layer at various angles of incidence so that total internal reflection conditions are satisfied at the interface; and a first photodetector means which detects the intensity of the first light beam reflected in total internal reflection at the interface of the first dielectric block and the first film layer, a reference unit comprising a second light source emitting a second light beam; a reference chip consisting of a second dielectric block transparent to the second light beam, a second film layer formed on one face of the second dielectric block and a second sample liquid holding system which holds a false sample liquid on the surface of the second film layer, the false sample liquid comprising said solvent; a sensing material which can be combined with said specific material in the sample liquid and is disposed on the second film layer; a second optical system which causes the second light beam to enter the second dielectric block to impinge upon the interface of the second dielectric block and the first film layer at various angles of incidence so that total internal reflection conditions are satisfied at the interface; and a second photodetector means which detects the intensity of the second light beam reflected in total internal reflection at the interface of the second dielectric block and the second film layer, and a measuring means which corrects result of detection by the first photodetector means on the basis of result of detection by the second photodetector means and measures the change of a state of attenuation in total internal reflection on the basis of the corrected result of detection by the first photodetector means, wherein the improvement comprises the steps of detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

In accordance with a second aspect of the present invention, the method of the present invention is applied to a surface plasmon resonance sensor. That is, in accordance with the second aspect of the present invention, there is provided a measuring method for detecting a state of attenuation in total internal reflection by the use of a measuring apparatus comprising a measuring unit comprising a first light source emitting a first light beam; a measuring chip consisting of a first dielectric block transparent to the first light beam, a first metal film formed on one face of the first dielectric block and a first sample liquid holding system which holds a sample liquid on the surface of the first metal film, the sample liquid comprising solvent and a sample; a sensing material which can be combined with a specific material in the sample liquid and is disposed on the first metal film; a first optical system which causes the first light beam to enter the first dielectric block to impinge upon the interface of the first dielectric block and the first metal film at various angles of incidence so that total internal reflection conditions are satisfied at the interface; and a first photodetector means which detects the intensity of the first light beam reflected in total internal reflection at the interface of the first dielectric block and the first metal film, a reference unit comprising a second light source emitting a second light beam; a reference chip consisting of a second dielectric block transparent to the second light beam, a second metal film formed on one face of the second dielectric block and a second sample liquid holding system which holds a false sample liquid on the surface of the second metal film, the false sample liquid comprising said solvent; a sensing material which can be combined with said specific material in the sample liquid and is disposed on the second metal film; a second optical system which causes the second light beam to enter the second dielectric block to impinge upon the interface of the second dielectric block and the first metal film at various angles of incidence so that total internal reflection conditions are satisfied at the interface; and a second photodetector means which detects the intensity of the second light beam reflected in total internal reflection at the interface of the second dielectric block and the second metal film, and a measuring means which corrects result of detection by the first photodetector means on the basis of result of detection by the second photodetector means and measures the change of a state of attenuation in total internal reflection due to generation of surface plasmon resonance on the basis of the corrected result of detection by the first photodetector means, wherein the improvement comprises the steps of detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

In accordance with a third aspect of the present invention, the method of the present invention is applied to a leaky mode sensor. That is, in accordance with the third aspect of the present invention, there is provided a measuring method for detecting a state of attenuation in total internal reflection by the use of a measuring apparatus comprising a measuring unit comprising a first light source emitting a first light beam; a measuring chip consisting of a first dielectric block transparent to the first light beam, a clad layer formed on one face of the first dielectric block, an optical waveguide layer which is formed on the clad layer and a first sample liquid holding system which holds a sample liquid on the surface of the clad layer, the sample liquid comprising solvent and a sample; a sensing material which can be combined with a specific material in the sample liquid and is disposed on the clad layer; a first optical system which causes the first light beam to enter the first dielectric block to impinge upon the interface of the first dielectric block and the clad layer at various angles of incidence so that total internal reflection conditions are satisfied at the interface; and a first photodetector means which detects the intensity of the first light beam reflected in total internal reflection at the interface of the first dielectric block and the clad layer, a reference unit comprising a second light source emitting a second light beam; a reference chip consisting of a second dielectric block transparent to the second light beam, a clad layer formed on one face of the second dielectric block, an optical waveguide layer which is formed on the clad layer and a second sample liquid holding system which holds a false sample liquid on the surface of the clad layer, the false sample liquid comprising said solvent; a sensing material which can be combined with said specific material in the sample liquid and is disposed on the clad layer; a second optical system which causes the second light beam to enter the second dielectric block to impinge upon the interface of the second dielectric block and the clad layer at various angles of incidence so that total internal reflection conditions are satisfied at the interface; and a second photodetector means which detects the intensity of the second light beam reflected in total internal reflection at the interface of the second dielectric block and the clad layer, and a measuring means which corrects result of detection by the first photodetector means on the basis of result of detection by the second photodetector means and measures the change of a state of attenuation in total internal reflection due to excitation of waveguide mode on the basis of the corrected result of detection by the first photodetector means, wherein the improvement comprises the steps of detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

In the methods in accordance with the first to third aspects of the present invention, the "difference in sensitivity between the measuring unit and the reference unit" may be detected, for instance, by causing the first and second light beams to impinge upon the interfaces at various angles of incidence so that total internal reflection conditions are satisfied at the interfaces with false sample liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit.

In accordance with fourth to sixth aspects of the present invention, there are provided measuring apparatuses respectively for carrying out the measuring methods in accordance with the first to third aspects of the present invention.

That is, in accordance with the fourth aspect of the present invention, there is provided a measuring apparatus utilizing the phenomenon of attenuation in total internal reflection comprising a measuring unit comprising a first light source emitting a first light beam; a measuring chip consisting of a first dielectric block transparent to the first light beam, a first film layer formed on one face of the first dielectric block and a first sample liquid holding system which holds a sample liquid on the surface of the first film layer, the sample liquid comprising solvent and a sample; a sensing material which can be combined with a specific material in the sample liquid and is disposed on the first film layer; a first optical system which causes the first light beam to enter the first dielectric block to impinge upon the interface of the first dielectric block and the first film layer at various angles of incidence so that total internal reflection conditions are satisfied at the interface; and a first photodetector means which detects the intensity of the first light beam reflected in total internal reflection at the interface of the first dielectric block and the first film layer, a reference unit comprising a second light source emitting a second light beam; a reference chip consisting of a second dielectric block transparent to the second light beam, a second film layer formed on one face of the second dielectric block and a second sample liquid holding system which holds a false sample liquid on the surface of the second film layer, the false sample liquid comprising said solvent; a sensing material which can be combined with said specific material in the sample liquid and is disposed on the second film layer; a second optical system which causes the second light beam to enter the second dielectric block to impinge upon the interface of the second dielectric block and the first film layer at various angles of incidence so that total internal reflection conditions are satisfied at the interface; and a second photodetector means which detects the intensity of the second light beam reflected in total internal reflection at the interface of the second dielectric block and the second film layer, and a measuring means which corrects result of detection by the first photodetector means on the basis of result of detection by the second photodetector means and measures the change of a state of attenuation in total internal reflection on the basis of the corrected result of detection by the first photodetector means, wherein the improvement comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

In accordance with the fifth aspect of the present invention, there is provided a measuring apparatus utilizing the phenomenon of attenuation in total internal reflection comprising a measuring unit comprising a first light source emitting a first light beam; a measuring chip consisting of a first dielectric block transparent to the first light beam, a first metal film formed on one face of the first dielectric block and a first sample liquid holding system which holds a sample liquid on the surface of the first metal film, the sample liquid comprising solvent and a sample; a sensing material which can be combined with a specific material in the sample liquid and is disposed on the first metal film; a first optical system which causes the first light beam to enter the first dielectric block to impinge upon the interface of the first dielectric block and the first metal film at various angles of incidence so that total internal reflection conditions are satisfied at the interface; and a first photodetector means which detects the intensity of the first light beam reflected in total internal reflection at the interface of the first dielectric block and the first metal film, a reference unit comprising a second light source emitting a second light beam; a reference chip consisting of a second dielectric block transparent to the second light beam, a second metal film formed on one face of the second dielectric block and a second sample liquid holding system which holds a false sample liquid on the surface of the second metal film, the false sample liquid comprising said solvent; a sensing material which can be combined with said specific material in the sample liquid and is disposed on the second metal film; a second optical system which causes the second light beam to enter the second dielectric block to impinge upon the interface of the second dielectric block and the first metal film at various angles of incidence so that total internal reflection conditions are satisfied at the interface; and a second photodetector means which detects the intensity of the second light beam reflected in total internal reflection at the interface of the second dielectric block and the second metal film, and a measuring means which corrects result of detection by the first photodetector means on the basis of result of detection by the second photodetector means and measures the change of a state of attenuation in total internal reflection due to generation of surface plasmon resonance on the basis of the corrected result of detection by the first photodetector means, wherein the improvement comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

In accordance with the sixth aspect of the present invention, there is provided a measuring apparatus utilizing the phenomenon of attenuation in total internal reflection comprising a measuring unit comprising a first light source emitting a first light beam; a measuring chip consisting of a first dielectric block transparent to the first light beam, a clad layer formed on one face of the first dielectric block, an optical waveguide layer which is formed on the clad layer and a first sample liquid holding system which holds a sample liquid on the surface of the clad layer, the sample liquid comprising solvent and a sample; a sensing material which can be combined with a specific material in the sample liquid and is disposed on the clad layer; a first optical system which causes the first light beam to enter the first dielectric block to impinge upon the interface of the first dielectric block and the clad layer at various angles of incidence so that total internal reflection conditions are satisfied at the interface; and a first photodetector means which detects the intensity of the first light beam reflected in total internal reflection at the interface of the first dielectric block and the clad layer, a reference unit comprising a second light source emitting a second light beam; a reference chip consisting of a second dielectric block transparent to the second light beam, a clad layer formed on one face of the second dielectric block, an optical waveguide layer which is formed on the clad layer and a second sample liquid holding system which holds a false sample liquid on the surface of the clad layer, the false sample liquid comprising said solvent; a sensing material which can be combined with said specific material in the sample liquid and is disposed on the clad layer; a second optical system which causes the second light beam to enter the second dielectric block to impinge upon the interface of the second dielectric block and the clad layer at various angles of incidence so that total internal reflection conditions are satisfied at the interface; and a second photodetector means which detects the intensity of the second light beam reflected in total internal reflection at the interface of the second dielectric block and the clad layer, and a measuring means which corrects result of detection by the first photodetector means on the basis of result of detection by the second photodetector means and measures the change of a state of attenuation in total internal reflection due to excitation of waveguide mode on the basis of the corrected result of detection by the first photodetector means, wherein the improvement comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

In the measuring apparatuses in accordance with the fourth to sixth aspects of the present invention, the sensitivity difference detecting means may be a means for detecting the "difference in sensitivity between the measuring unit and the reference unit", for instance, by causing the first and second light beams to impinge upon the interfaces at various angles of incidence so that total internal reflection conditions are satisfied at the interfaces with false sample liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit.

Though it is preferred that the "false sample liquid" solely comprises the same solvent used in the sample liquid, but need not be so. For example, a liquid which is substantially the same in characteristics of action with the sensing material and/or the optical characteristics as the solvent used in the sample liquid may be used as the false sample liquid.

The sensing material and the specific material in the sample liquid may be combined each other, for instance, by interaction between proteins, interaction between DNA and protein, interaction between sugar and protein, interaction between protein and peptide, interaction between fat and protein or chemical reactions.

The first and second light sources may be either separate light sources or a single light source common to the measuring unit and the reference unit. The first and second optical systems may be either separate optical systems or a single optical system common to the measuring unit and the reference unit. The first and second photodetector means may be either separate photodetector means or a single photodetector means common to the measuring unit and the reference unit.

In accordance with the measuring methods and the measuring apparatuses in accordance with the first to sixth aspects of the present invention, since the difference in sensitivity between the measuring unit and the reference unit is detected before initiating the measurement of the change of a state of attenuation in total internal reflection, and result of measurement by the measuring means is calibrated on the basis of the difference in sensitivity between the measuring unit and the reference unit, influence of the difference in sensitivity between the measuring unit and the reference unit on the measuring accuracy can be suppressed and the accuracy in measurement of the change of a state of attenuation in total internal reflection can be improved.

When the "difference in sensitivity between the measuring unit and the reference unit" is detected by causing the first and second light beams to impinge upon the interfaces at various angles of incidence so that total internal reflection conditions are satisfied at the interfaces with false sample liquids held by the sample holding liquid systems of the respective units, detecting changes of the state of the attenuation in total internal reflection on the basis of the intensities of the light beams reflected at the interfaces by the measuring unit and the reference unit and comparing results of detection by the measuring unit and the reference unit, influence of the sensitivity difference between the measuring chip and the reference chip and/or the sensitivity difference between the photodetector means of the measuring unit and the reference unit can be suppressed and the accuracy in measuring the state of combination between the sensing material and the sample can be improved.

In accordance with a seventh aspect of the present invention, there is provided a measuring method for analyzing a sample by the use of a measuring apparatus comprising; a measuring chip consisting of a dielectric block, a film layer formed on one face of the dielectric block and a sample holding system which holds the sample on the surface of the film layer; a light source which emits a light beam; an optical system which causes the light beam to enter the dielectric block at an angle of incidence such that total internal reflection conditions are satisfied at the interface of the dielectric block and the film layer; and a photodetector means which detects the intensity of the light beam reflected in total internal reflection at the interface, wherein the improvement comprises the steps of measuring the refractive indexes of a plurality of reference samples whose refractive indexes are known, thereby obtaining a calibration standard on the basis of result of measurement on the reference samples, and calibrating result of measurement on the sample on the basis of the calibration standard.

In accordance with an eighth aspect of the present invention, there is provided a measuring apparatus comprising; a measuring chip consisting of a dielectric block, a film layer formed on one face of the dielectric block and a sample holding system which holds the sample on the surface of the film layer; a light source which emits a light beam; an optical system which causes the light beam to enter the dielectric block at an angle of incidence such that total internal reflection conditions are satisfied at the interface of the dielectric block and the film layer; and a photodetector means which detects the intensity of the light beam reflected in total internal reflection at the interface, wherein the improvement comprises a calibrating means which obtains a calibration standard by measuring the refractive indexes of a plurality of reference samples whose refractive indexes are known and calibrates result of measurement on the sample on the basis of the calibration standard.

The seventh and eighth aspects of the present invention can be applied to, for instance, a surface plasmon resonance sensor where the film layer is a metal film and a leaky mode sensor where the film layer comprises a clad layer formed on one face of the dielectric block and an optical waveguide layer formed on the clad layer.

In the measuring apparatuses of the seventh and eighth aspects of the present invention, the sample may be analyzed in various ways on the basis of the intensity of the light beam reflected in total internal reflection at the interface. For example, the sample may be analyzed by detecting the position (angle) of a dark line generated by attenuation in total internal reflection by causing the light beam to impinge upon the interface so that total internal reflection conditions are satisfied at the interface and various angles of incidence of the light beam to the interface are obtained, and measuring the intensity of the light beam reflected in total internal reflection at the interface by positions corresponding to angles of incidence, or by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS XIII, 1999, pp.585–588).

In the seventh and eighth aspects of the present invention, it is preferred that the measuring apparatus further comprises a reference sample generating means which mixes two samples, whose refractive indexes (dielectric constants) are known, in different proportions to generate a plurality of reference samples whose refractive indexes are between the refractive indexes of said two samples whose refractive indexes are known.

The reference samples need not be liquid but may be, for instance, solid. For example, the "refractive indexes of a plurality of reference samples whose refractive indexes are known" may be obtained by the use of a measuring chip (a calibration jig) where a solid material of a known refractive index (dielectric constant) is fixed (e.g., by deposition) on the film layer.

In this case, it is preferred that the calibration jig comprises a plurality of measuring chips which are arranged in a row and integrated with each other into a measuring chip unit and a plurality of solid materials whose refractive indexes are known and which are respectively fixed on the film layers of the measuring chips. In such a measuring chip unit, the dielectric blocks of the respective measuring chips may be formed integrally.

Further, it is preferred that the photodetector means comprises a plurality of photodetector elements which are arranged in a predetermined direction to receive the light beam reflected at the interface in total internal reflection, a differential means which differentiates detecting signals output from the photodetector elements in the direction in which the photodetector elements are arranged and outputs the differentials obtained, and a measuring means which subtracts from a differential, close to a point at which change of the detecting signal in the direction in which the photodetector elements are arranged changes from decrease to increase, the initial value of the differential and measures the change with time of the differential.

Though, it is preferred that the "differential close to a point at which change of the detecting signal in the direction in which the photodetector elements are arranged changes from decrease to increase" be the differential closest to the point, it need not be necessarily so but may be any one close to the point. Further, the "initial value of the differential" may be either a differential which is obtained for the first time after measurement is initiated and is close to a point at which change of the detecting signal in the direction in which the photodetector elements are arranged changes from decrease to increase, or a value set as an initial value by carrying out an operation such as feedback for shifting a measured value at the beginning of measurement to a value close to 0. The measuring means may subtract "from a differential, close to a point at which change of the detecting signal in the direction in which the photodetector elements are arranged changes from decrease to increase, the initial value of the differential", for instance, by the use of a subtracter or a differential circuit.

In accordance with the seventh and eighth embodiments of the present invention, since the refractive indexes of a plurality of reference samples whose refractive indexes are known are measured, thereby obtaining a calibration standard on the basis of result of measurement on the reference samples, and result of measurement on the sample is calibrated on the basis of the calibration standard, the difference in sensitivity among measuring apparatuses can be suppressed and the sample can be analyzed more accurately.

BRIEF DESCRIPTION OF THE DRAWINGS

FIG. 1 is a side view of a surface plasmon resonance sensor in accordance with a first embodiment of the present invention, FIG. 2 is a block diagram showing the electrical arrangement of the surface plasmon resonance sensor of the first embodiment.

DESCRIPTION OF THE PREFERRED EMBODIMENTS

Figure 3A:
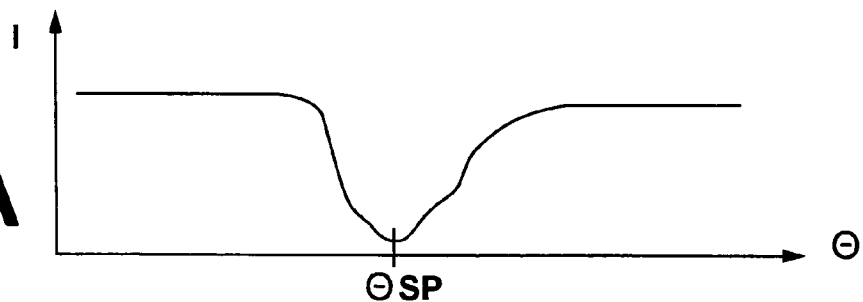
FIG. 3A shows an example of the relation between the intensity I of the component of the laser beam reflected in total internal reflection at the interface and the angle of incidence θ of the component.

FIG. 1 shows a measuring apparatus in the form of a surface plasmon resonance sensor in accordance with a first embodiment of the present invention. In the surface plasmon resonance sensor of this embodiment, a false sample liquid is supplied to the measuring chip and the reference chip which have been provided with a sensing material, and the change of the attenuation angle θsp is measured, whereby the difference in sensitivity between the measuring unit and the reference unit is measured. Thereafter, a sample material is provided only to the measuring chip and whether the sensing material is combined with the sample material is actually measured. Then whether the sample material is a specific material is judged. This judgment is done on the basis of calibrated data obtained by calibrating the data obtained by the actual measurement on the basis of the data obtained by the sensitivity difference measurement.

As shown in FIG. 1, the surface plasmon resonance sensor of this embodiment comprises a measuring unit 5, a reference unit 5' a signal processing section 20 which may be, for instance, a computer system and receives result of measurement from the measuring unit 5 and the reference unit 5', and a display 21 connected to the signal processing section 20.

The measuring unit 5 comprises a disposable measuring chip 6 comprising a dielectric block 10 which is like a truncated pyramid in shape and a metal film 12 of gold, silver, copper, aluminum or the like formed on one face of the dielectric block 10.

The dielectric block 10 is formed, for instance, of transparent synthetic resin and the metal film 12 is provided on the bottom of a recessed portion 10a, which functions as a sample holding well for holding a sample liquid 11. In this particular embodiment, a sensing medium 30, which will be described later, is fixed on the metal film 12.

The disposable measuring chip 6 is fixed in a chip holding hole 31a provided in a turn table 31. The measuring chip 6 further comprises a laser 14 (e.g., a semiconductor laser) emitting a single laser beam 13, an incident optical system 15 which causes the laser beam 13 to enter the dielectric block 10 so that total internal reflection conditions are satisfied at the interface 10b of the dielectric block and the metal film 12 and various angles of incidence of the light beam to the interface of the dielectric block 10 and the metal film 12 can be obtained, a collimator lens 16 which converts the laser beam 13 reflected in total internal reflection at the interface 10b into a parallel laser beam, a photodiode array 17 which detects the parallel laser beam 13, a differential amplifier array 18 connected to the photodiode array 17, and a driver 19.

The reference unit 5' is of the substantially same structure as the measuring unit 5 and comprises a disposable reference chip 6' having a dielectric block 10 and a metal film 12. A false sample liquid 11' comprising the solvent of the sample liquid 11 is supplied to the reference chip 6'. FIG. 2 shows the electrical arrangement of each of the measuring unit 5 and the reference unit 5'. As shown in FIG. 2, the driver 19 comprises sample hold circuits 22a, 22b, 22c . . . which sample-hold the outputs of the respective differential amplifiers 18a, 18b, 18c . . . of the differential amplifier array 18, a multiplexer 23 into which the outputs of the sample hold circuits 22a, 22b, 22c . . . are input, an A/D convertor 24 which digitizes the outputs of the multiplexer, 23 and inputs them into the signal processing section 20, a drive circuit 25 which drives the multiplexer 23 and the sample hold circuits 22a, 22b, 22c . . . , and a controller 26 which controls the drive circuit 25 under the control of the signal processing section 20.

The signal processing section 20 is provided with a sensitivity difference detecting section 4 which carries out sensitivity difference measurement for obtaining the difference in sensitivity between the measuring unit 5 and the reference unit 5' and stores the sensitivity difference, and judges whether the sample material is a specific material is judged on the basis of calibrated data obtained by calibrating the data obtained by the actual measurement on the basis of the sensitivity difference stored in the sensitivity difference detecting section 4.

As shown in FIG. 1, the laser beam 13 emitted from the laser 14 as a divergent light beam is converged on the interface 10b of the dielectric block 10 and the metal film 12 by the incident optical system 15. As described above, the laser beam 13 includes components impinging upon the interface at various angles of incidence θ not smaller than the angle of total internal reflection. Accordingly, the laser beam 13 is reflected in total internal reflection at the interface 10b and the reflected laser beam 13 includes components reflected at the interface 10b at various angles of reflection.

The laser beam 13 is caused to impinge upon the interface 10b in a p-polarized state. This can be realized by positioning the laser 14 so that the laser beam 13 impinges upon the interface 10b in a p-polarized state. Otherwise, the direction of polarization of the laser beam 13 may be controlled by a wavelength plate.

The laser beam 13 reflected in total internal reflection at the interface 10b is detected by the photodiode array 17 after collimated by the collimator lens 16. In this particular embodiment, the photodiode array 17 comprises a plurality of photodiodes 17a, 17b, 17c . . . are arranged in a row in a direction substantially normal to the direction of travel of the collimated laser beam 13 in a plane of FIG. 1. That is, the components of the reflected laser beam 13 impinge upon different photodiodes 17a, 17b, 17c . . . .

The outputs of adjacent pairs of the photodiodes 17a, 17b, 17c . . . are respectively input into the differential amplifiers 18a, 18b, 18c . . . of the differential amplifier array 18. Accordingly, the outputs of the differential amplifiers 18a, 18b, 18c . . . of the differential amplifier array 18 represents differentials of the outputs of the photodiodes 17a, 17b, 17c . . . (representing the intensities of light which they detect) in the direction in which the photodiodes 17a, 17b, 17c . . . are arranged.

The outputs of the differential amplifiers 18a, 18b, 18c . . . are sample-held at predetermined timings by the respective sample hold circuits 22a, 22b, 22c . . . and input into the multiplexer 23. The multiplexer 23 inputs the outputs of the respective sample hold circuits 22a, 22b, 22c . . . into the A/D convertor 24 in a predetermined order. The A/D convertor 24 digitizes the outputs of the respective sample hold circuits 22a, 22b, 22c . . . and inputs them into the signal processing section 20.

FIG. 3A shows an example of the relation between the intensity I of the component of the laser beam 13 reflected in total internal reflection at the interface 10b and the angle of incidence θ of the component.

A component of the laser beam 13 impinging upon the interface 10b at a particular angle of incidence θsp excites surface plasmon in the interface 10b between the metal film 12 and the sample liquid 11 and the intensity I of the component reflected in total internal reflection at the interface 10b sharply drops. That is, the particular angle of incidence is the attenuation angle θsp and the intensity I of the reflected laser beam 13 is minimized at the attenuation angle θsp. The sharp drop of the reflected laser beam 13 is observed as a dark line as indicated at D in FIG. 1.

Figure 3B:
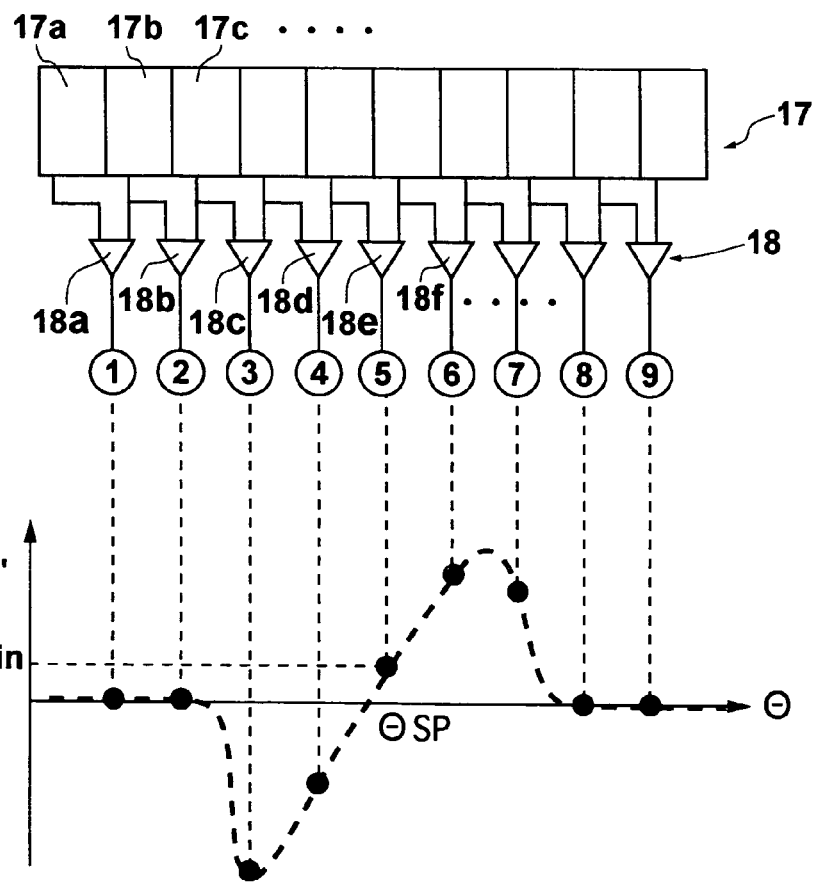
FIG. 3B is a view showing the relation between the differentials I' of the intensities I of the reflected laser beam and the angle of incidence θsp.

As shown in FIG. 3B, the positions of the photodiodes 17a, 17b, 17c . . . in the direction in which they are arranged are one-to-one correspondence with the angle of incidence θsp.

FIG. 3B also shows the relation between the output I' of the differential amplifier (the differential of the intensities I of the reflected laser beam 13) and the position of the photodiode 17a, 17b, 17c . . . in the direction in which the photodiodes are arranged (or the angle of incidence θsp).

Prior to measurement, the signal processing section 20 sets an initial value I' r of the differential I'. The signal processing section 20 selects one of the differential amplifiers 18a, 18b, 18c . . . whose output I' takes a value I' min closest to 0 corresponding to the attenuation angle θsp (where the change of the intensity I of the reflected laser beam 13 changes from decrease to increase) on the basis of the differentials I' input from the A/D convertor 24 (the differential amplifier 18e in the particular example shown in FIG. 4B).

The differential I' min is input into the signal processing section 20 from the differential amplifier 18e and the differential I' min is stored in a memory (not shown). Thereafter, each time a predetermined time lapses, the value of the differential I' min output from the differential amplifier 18e is measured and the change Δ I' of the differential I' is calculated by subtracting the initial value I' r from the differential I'. Initially, the change ΔI' of the differential I' is substantially 0 irrespective of the value of the differential I' output from the differential amplifier 18e.

The differential I' increases and decreases with left and right movement of the curve shown in FIG. 3A which takes place with change of the dielectric constant or the refractive index of the material in contact with the metal film 12 of the measuring chip. Accordingly, when the differential I' is kept measured, change with time of the attenuation angle θsp can be detected and change of the refractive index of the sensing material 30 in contact with the metal film 12 can be known on the basis of the change with time of the attenuation angle θsp.

That is when the sensing medium 30 is a material which combines with a specific material (the sample) in the sample liquid 11, the refractive index of the sensing medium 30 changes depending on the state of combination of the sensing medium 30 and the specific material, change of the state of combination of the sensing medium 30 and the specific material can be detected by keeping measuring the change ΔI' of the differential I'.

Figure 4:
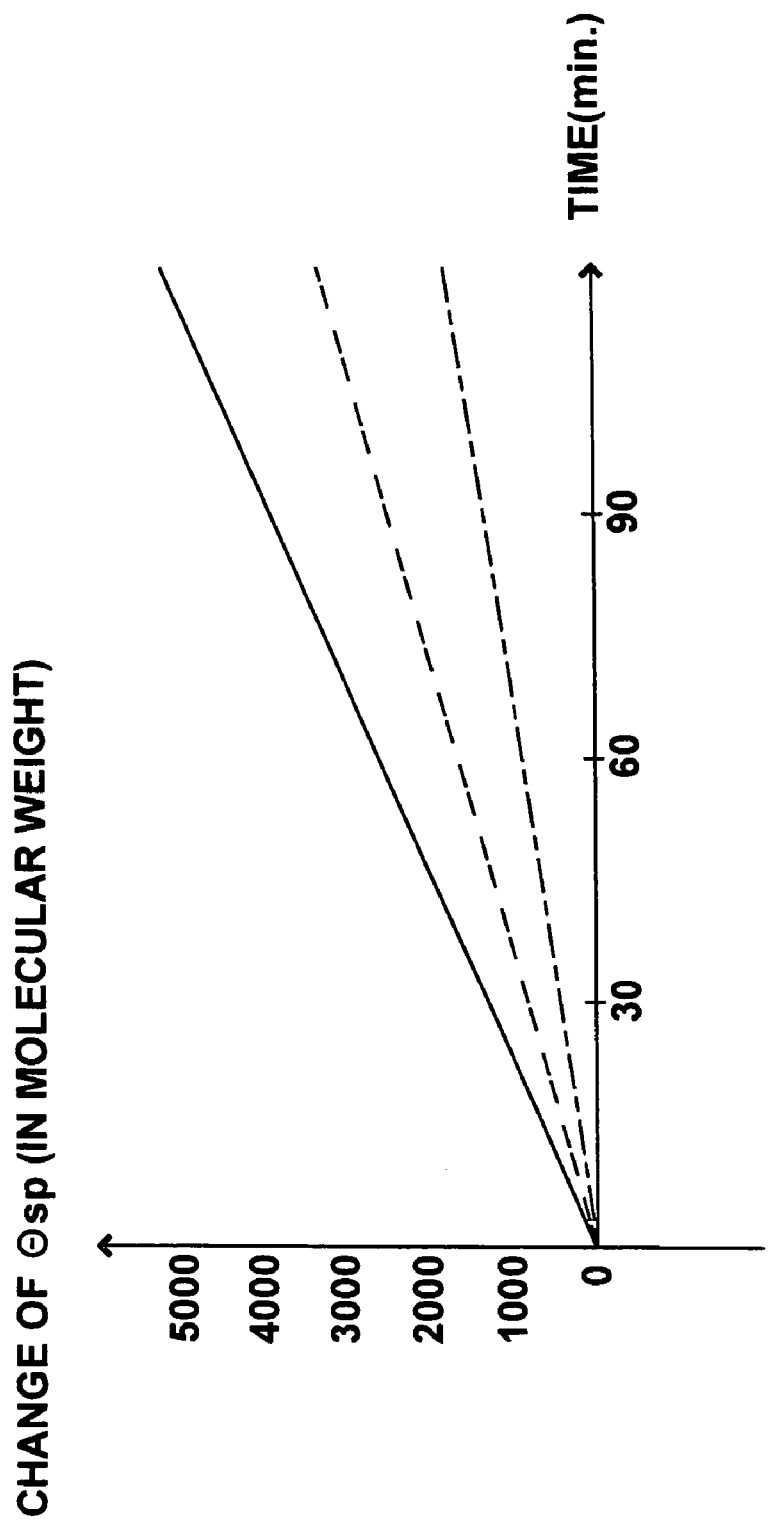
FIG. 4 is a graph showing the sensitivity difference.

Measurement of the sensitivity difference and actual measurement will be described, hereinbelow. In measurement of the sensitivity difference, a false sample liquid is supplied to the measuring chip 6 and the reference chip 6' which have been provided with a sensing medium, and changes of the attenuation angle θsp, that is, changes ΔI' of the differential I', as measured by the measuring unit 5 and the reference unit 5' are measured at predetermined time intervals for one hour. The sensitivity difference detecting section 4 calculates the difference in sensitivity between the measuring unit 5 and the reference unit 5' on the basis of result of measurement of the sensitivity difference and stores the difference in sensitivity. For example, when the result of measurement by the reference unit 5' is as shown by the broken line in FIG. 4 and the result of measurement by the measuring unit 5 is as shown by the solid line in FIG. 4, the sensitivity difference detecting section 4 determines the sensitivity of the measuring unit 5 is 1.6 times as high as that of the reference unit 5' and stores the value. FIG. 4 shows change of the attenuation angle θsp in terms of molecular weight of the sample material obtained from the change ΔI' of the differential I'.

In actual measurement, a sample liquid 11 comprising a small amount of solvent and a sample material dissolved in the solvent is spotted onto the measuring chip 6 and the solvent is spotted onto the reference chip 6' in the same amount and at the same temperature. Then changes ΔI' of the differential I' as measured by the measuring unit 5 and the reference unit 5' are measured at predetermined time intervals.

The signal processing section 20 multiplies the change Δ I' of the differential I', or the change of the attenuation angle θsp, as measured by the reference unit 5' by 1.6, thereby calibrating the change ΔI' of the differential I' as measured by the reference unit 5'. Then the signal processing section 20 subtracts the calibrated change ΔI' of the attenuation angle θsp as measured by the reference unit 5' from the change ΔI' of the attenuation angle θsp as measured by the measuring unit 5 and obtains a corrected change of the attenuation angle θsp.

Figure 5:
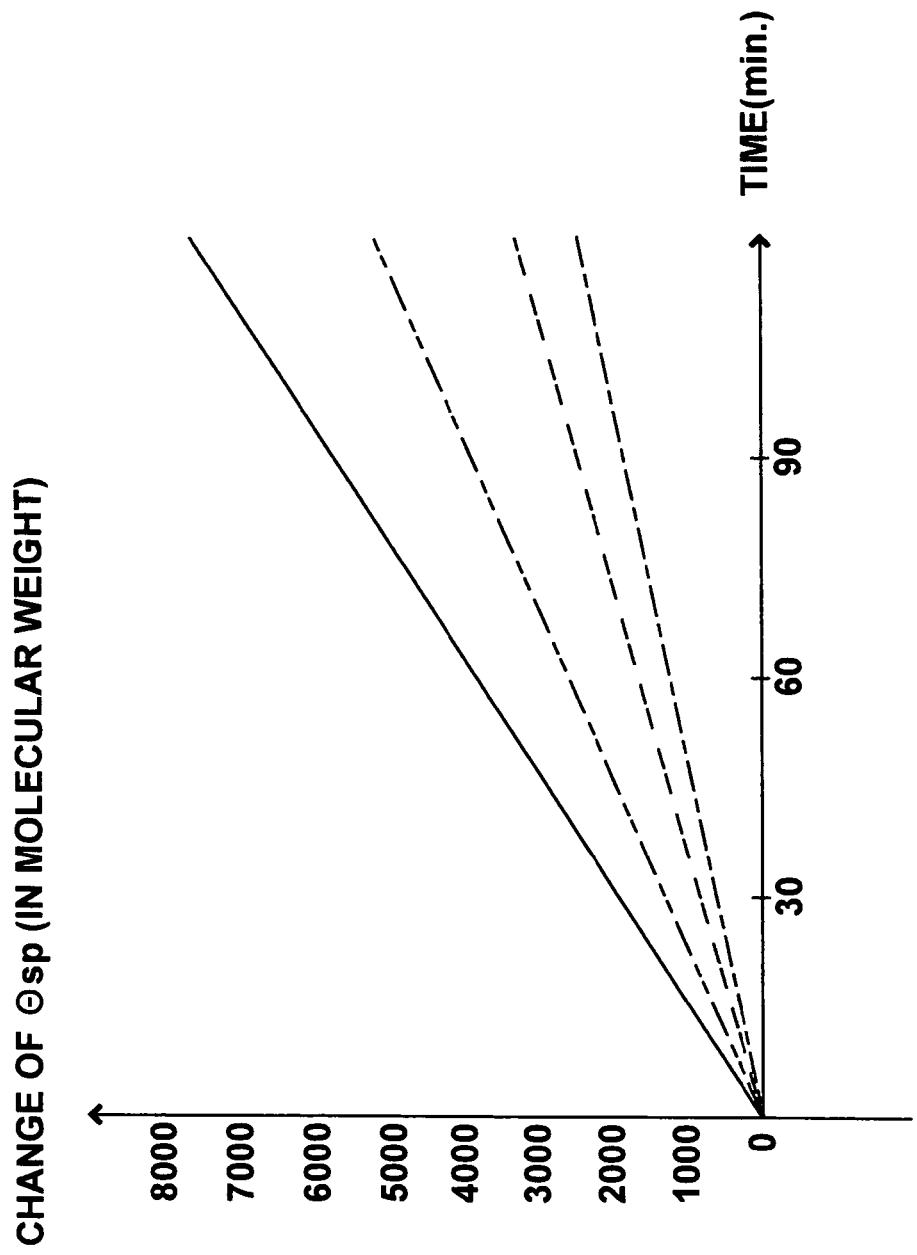
FIG. 5 is a graph showing the corrected change of the attenuation angle θsp.

For example, when the change of the attenuation angle θsp as measured by the reference unit 5' in actual measurement is as shown by the broken line in FIG. 5 and the change of the attenuation angle θsp as measured by the measuring unit 5 in sensitivity difference measurement is as shown by the solid line in FIG. 5, the calibrated change ΔI' of the attenuation angle θsp as measured by the reference unit 5' is as shown by the double-dotted chained line in FIG. 5 and the corrected change of the attenuation angle θsp is as shown by the single-dotted chained line in FIG. 5. The signal processing section 20 judges the state of combination of the sensing medium 30 and the sample material on the basis of the corrected change of the attenuation angle θsp. When the temperature of the sample liquid 11 added to the measuring chip 6 differs from the temperature of the sample liquid 11 which has been in the measuring chip 6, a temperature change can take place, which can vary the change ΔI' of the differential I'. In this particular embodiment, since the solvent is supplied to the reference chip 6' in the same amount and at the same temperature, variations in the changes ΔI' of the differential I' due to the temperature change are compensated upon correction and cannot affect the measuring accuracy. Similarly, variations in the changes ΔI' of the differential I' due to, for instance, the environmental temperature change are also compensated upon correction.

As can be understood from the description above, in this embodiment, since the difference in sensitivity between the measuring unit 5 and the reference unit 5' is detected, and change of the state of attenuation in total internal reflection is judged on the basis of the corrected change of the attenuation angle θsp corrected on the basis of the difference in sensitivity, influence of the sensitivity difference between the measuring unit 5 and the reference unit 5' can be suppressed and the accuracy in measuring the state of combination between the sensing material and the sample can be improved.

Further, since the difference in sensitivity of the measuring unit 5 and the reference unit 5' is detected by detecting changes of the state of total internal reflection by the measuring unit 5 and the reference unit 5' with the false sample liquid held by the measuring chip 6 and the reference chip 6' and comparing the results of detection by the units 5 and 5', influence of the difference in sensitivity between the measuring unit 6 and the reference unit 6', due to difference in thickness of the metal film 12 between the measuring chip 6 and the reference chip 6' and/or the difference in sensitivity of the photodiode array 17, on the measuring accuracy can be suppressed and the accuracy in measurement of the change of a state of combination of the sensing medium and the sample material can be improved.

The sensitivity difference between the measuring unit 5 and the reference unit 5' may be detected by changing the refractive index of the false sample liquid itself. Detection of the sensitivity difference in the case where a PBS (phosphoric acid buffer solution) containing therein 1% of DMSO (dimethyl sulfoxide) is employed will be briefly described by way of example. A predetermined amount of PBS containing therein 2% of DMSO is supplied to each of the measuring chip 6 and the reference chip 6' provided with a sensing material 30 and a first measurement is carried out. Then PBS is added to the measuring chip 6 and the reference chip 6' in the same amount as the liquid first supplied to each of the measuring chip 6 and the reference chip 6' and a second measurement is carried out.

In the second measurement, the false sample liquid in each of the measuring chip 6 and the reference chip 6' is diluted to a PBS containing therein 1% of DMSO, and accordingly the false sample liquid used in the first measurement differs from the false sample liquid used in the second measurement in refractive index, and the attenuation angle θsp as measured in the first measurement differs from that as measured in the second measurement. By measuring changes of the attenuation angle θsp measured by each unit in the first and second measurements, that is, changes Δ I' of the differential I', the sensitivity difference between the measuring unit 5 and the reference unit 5' can be calculated. Further, since PBS containing therein 1% of DMSO has been supplied to each chip upon the end of the sensitivity difference measurement, the actual measurement can be carried out immediately after the end of the sensitivity difference measurement.

When the sensitivity difference between the measuring unit 5 and the reference unit 5' is detected by changing the refractive index of the false sample liquid, the sensitivity difference can be detected in a short time and at the same time can be detected by the use of a measuring chip 6 and a reference chip 6' which are not provided with a sensing material. In the latter case, actual measurement is carried out after providing the chips with a sensing material after the sensitivity difference measurement.

Figure 6:
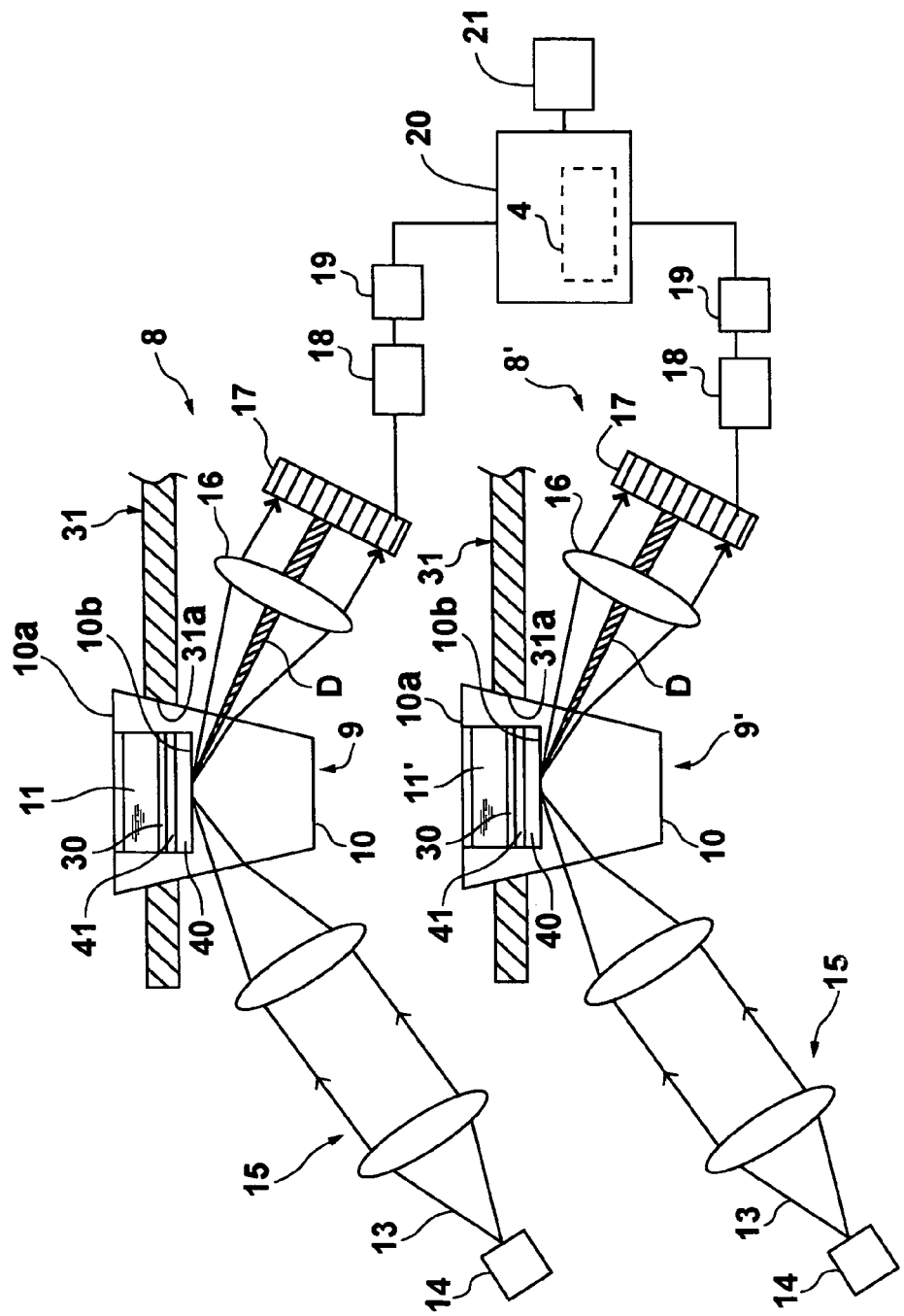
FIG. 6 is a side view of a leaky mode sensor in accordance with a second embodiment of the present invention.

A second embodiment of the present invention will be described with reference to FIG. 6, hereinbelow. In FIG. 6, the elements analogous to those shown in FIG. 1 are given the same reference numerals and will not be described here.

The measuring apparatus of the second embodiment is substantially the same as that of the first embodiment except that the former is a leaky mode sensor and the latter is a surface plasmon resonance sensor. That is, in the leaky mode sensor of the second embodiment, a measuring unit 8 including a measuring chip 9 and a reference unit 8' including a reference chip 9' are employed.

The dielectric block 10 of the measuring unit 8 and the reference unit 8' is formed of synthetic resin or optical glass (e.g., BK7), and a clad layer 40 is formed on one face of the dielectric block 10 and an optical waveguide layer 41 is formed on the clad layer 40. The clad layer 40 is in the form of film of dielectric material or metal (e.g., gold) which is lower in refractive index than the dielectric block 10. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the laser beam 13 emitted from the laser 14 is caused to impinge upon the clad layer 40 through the dielectric block 10 at an angle not smaller than an angle of total internal reflection, only light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface of the dielectric block 10 and the clad layer 40 sharply drops. That is, attenuation in total internal reflection occurs.

Since the wave number of light to be propagated through the optical waveguide layer 41 in a waveguide mode depends upon the refractive index of the sensing medium 30 on the optical waveguide layer 41, the refractive index of the sensing medium 30 can be detected on the basis of the differentials I' output from each of the differential amplifiers of the differential amplifier array 18.

Also in this embodiment, the signal processing section 20 carries out the sensitivity difference measurement and the actual measurement and carries out calibration and correction in the manner similar to those in the first embodiment. That is, result of measurement by the reference unit 8' is calibrated on the basis of the sensitivity difference and result of measurement by the measuring unit 8 is corrected on the basis of the calibrated result of measurement by the reference unit 8', and the change of the state of attenuation in total internal reflection is detected on the basis of the corrected result of measurement by the measuring unit 8.

Though, in the embodiments described above, the sensitivity difference is measured with the measuring chip supplied with a false sample liquid and then the sample material is added to the false sample liquid (solvent) when actual measurement is to be carried out, a sample liquid containing therein a sample material may be supplied to the measuring chip after the false sample liquid in the measuring chip is discarded. In this case, it is preferred that the false sample liquid in the reference chip be replaced by new false sample liquid.

Figure 7:
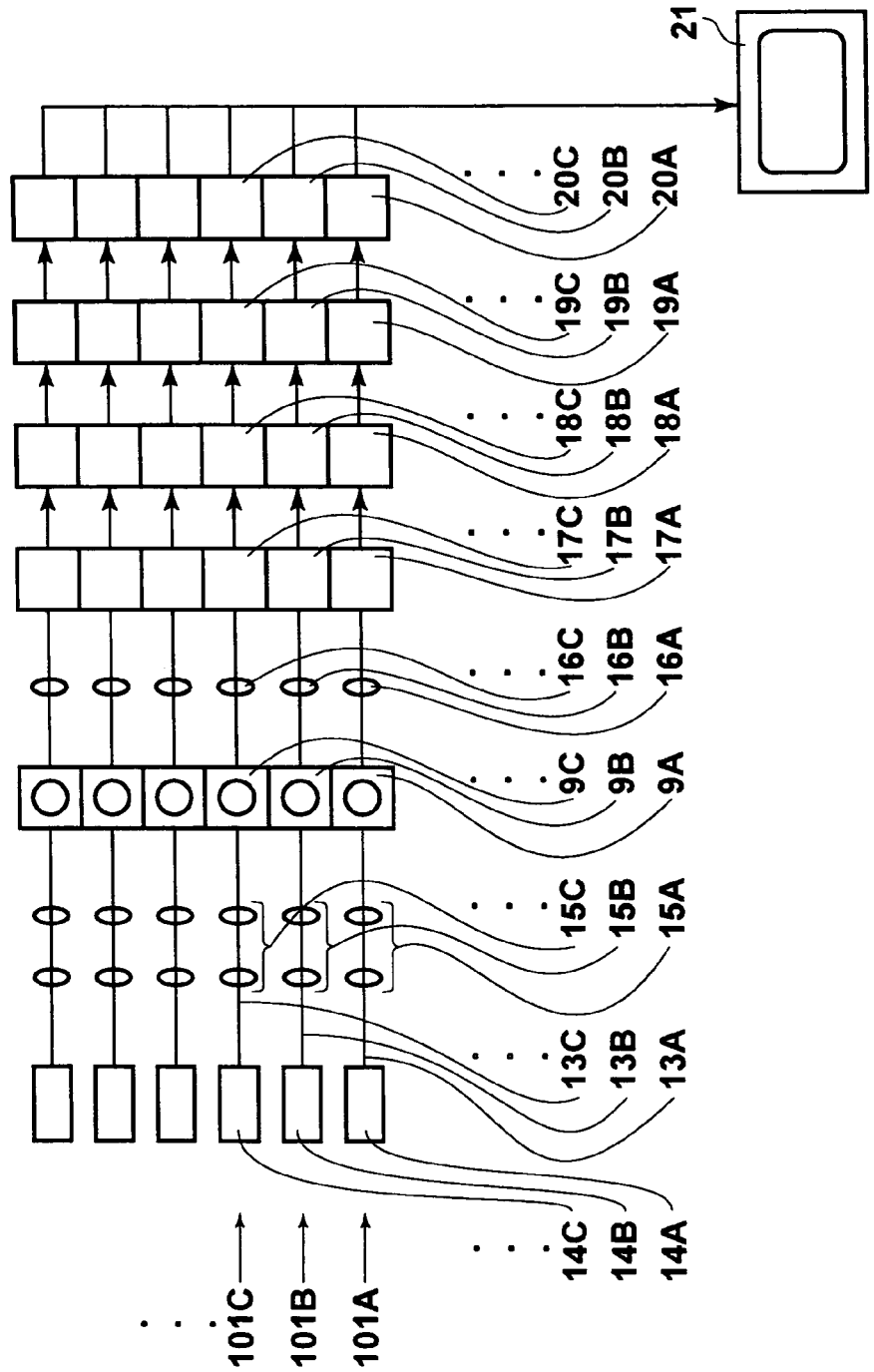
FIG. 7 is a plan view showing a surface plasmon resonance sensor in accordance with a third embodiment of the present invention.

FIG. 7 shows a surface plasmon resonance sensor 101 in accordance with a third embodiment of the present invention. In the third embodiment, elements analogous to those in the first embodiment are given the same numerals. The surface plasmon resonance sensor 101 is a provided with a plurality of measuring units 101A, 101B, 101C . . . of the same structure and can analyze a plurality of samples at one time.

The measuring units will be described, hereinbelow, with the suffixed alphabet (e.g., A, B, C) removed from the reference numerals of the respective elements. Each measuring unit 101 comprises a measuring chip 9, a laser source 14 which emits a laser beam 13, an incident optical system 15 which causes the laser beam 13 to impinge upon an interface 10b between a dielectric block 12 and a metal film 12, a collimator lens 16 which converts the laser beam 13 reflected in total internal reflection at the interface 10b into a parallel laser beam, a photodetector means 17 which detects the intensity of the parallel laser beam 13 passing through the collimator lens 16, a differential amplifier array 18 connected to the photodetector means 17, a driver 19 connected to the differential amplifier array 18, and a signal processing section (CPU) 20 which may comprise, for instance, a computer system and is connected to the driver 19. The signal processing section 20 has a built-in memory (not shown) which stores data on result of reference measurement in calibration (to be described later).

Figure 9:
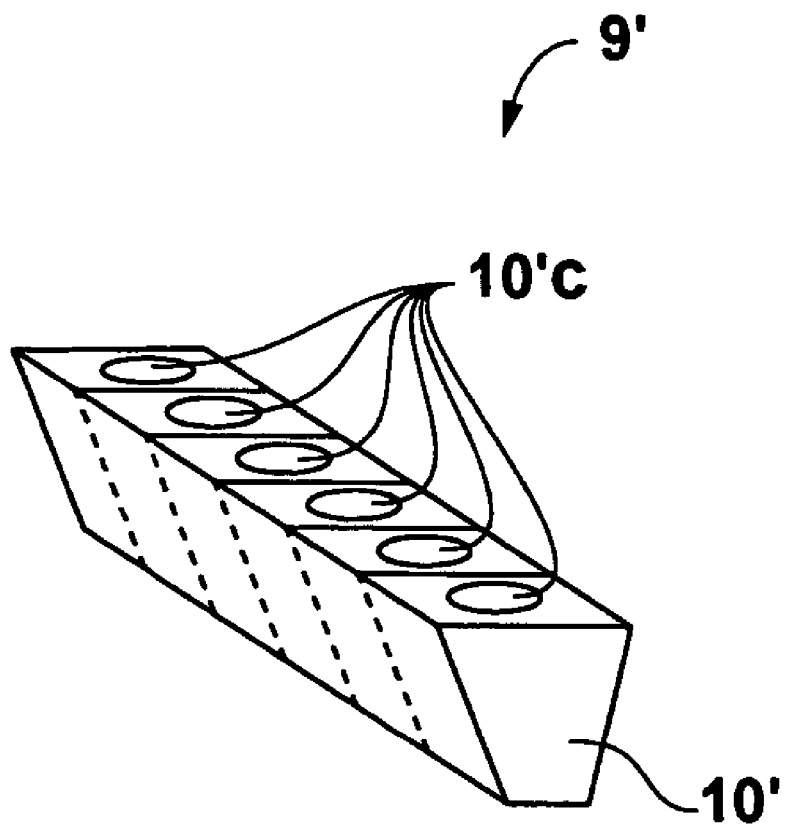
FIG. 9 is a view showing a modification of the measuring chip employed in the surface plasmon resonance sensor of the third embodiment.

The measuring chip 9 comprises a dielectric block 10 which is like a truncated pyramid in shape and a metal film 12 of gold, silver, copper, aluminum or the like is formed on one face of the dielectric block 10. The dielectric block 10 is formed, for instance, of transparent synthetic resin and the metal film 12 is provided on the bottom of a recessed portion 10a, which functions as a sample holding well for holding a sample liquid 11. A sensing medium 30, which will be described later, may be fixed on the metal film 12. The dielectric blocks of measuring chips of a plurality of measuring units may be integrated as a modification shown in FIG. 9. In FIG. 9, reference numeral 10' denotes a dielectric block and reference numeral 10'c denotes a recessed portion of the modification.

The incident optical system 15 comprises a collimator lens 15a which converts the laser beam 13, emitted from the laser 14 as a divergent light beam, into a parallel laser beam, and a condenser lens 15b which converges the collimated laser beam 13 on the interface 10b.

Since converged by the condenser lens 15b as described above, the laser beam 13 includes components impinging upon the interface at various angles of incidence θ. The laser 14 and the incident optical system 15 are arranged so that the angles of incidence θ are all not smaller than the angle of total internal reflection. Accordingly, the laser beam 13 is reflected in total internal reflection at the interface 10b and the reflected laser beam 13 includes components reflected at the interface 10b at various angles of reflection. The incident optical system 15 may be arranged to cause the laser beam 13 to impinge upon the interface 10b in a defocused state. This arrangement causes the laser beam 13 to be reflected at the interface 10b over a wider area thereof and averages errors in detecting states of surface plasmon resonance and improves measuring accuracy.

The laser beam 13 is caused to impinge upon the interface 10b in a p-polarized state. This can be realized by positioning the laser 14 so that the laser beam 13 impinges upon the interface 10b in a p-polarized state. Otherwise, the direction of polarization of the laser beam 13 may be controlled by a wavelength plate.

The surface plasmon resonance sensor 101 of this embodiment further comprises a display 21 connected to the signal processing sections 20A, 20B, 20C . . . of the measuring units.

Analysis of a sample by the surface plasmon resonance sensor of this embodiment will be described, hereinbelow.

Figure 8:
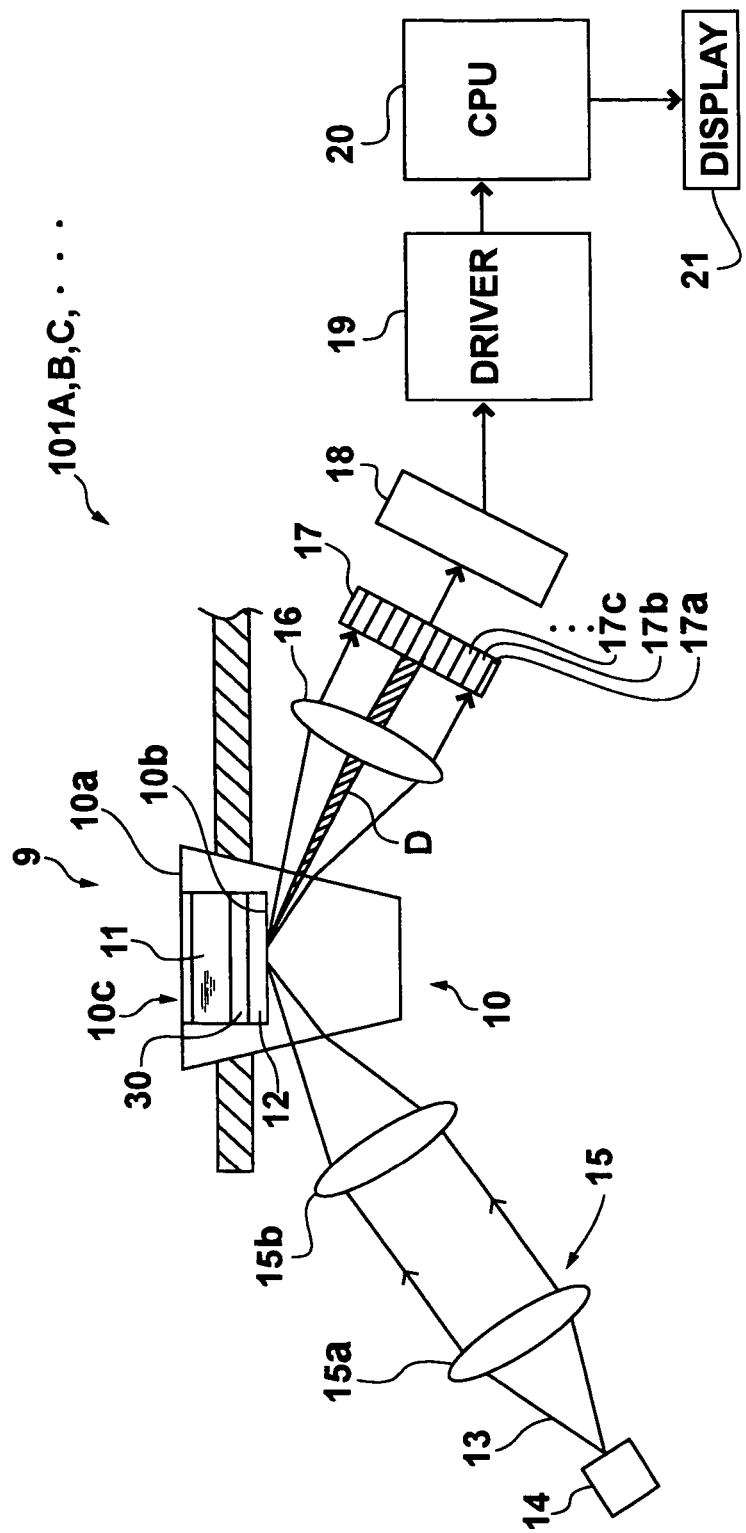
FIG. 8 is a side view of the surface plasmon resonance sensor of the third embodiment.

As shown in FIG. 8, the laser beam 13 emitted from the laser 14 as a divergent light beam is converged on the interface 10b of the dielectric block 10 and the metal film 12 by the incident optical system 15.

The laser beam 13 reflected in total internal reflection at the interface 10b is detected by the photodetector means 17 after collimated by the collimator lens 16. In this particular embodiment, the photodetector means 17 is a photodiode array in which a plurality of photodiodes 17a, 17b, 17c . . . are arranged in a row substantially in parallel to the surface of FIG. 8 in a direction substantially normal to the direction of travel of the collimated laser beam 13 in a plane of FIG. 8. That is, the components of the reflected laser beam 13 impinge upon different photodiodes 17a, 17b, 17c . . . and the photodetector means outputs a signal representing the intensity distribution in the laser beam 13.

A component of the laser beam 13 impinging upon the interface 10b at a particular angle of incidence θsp excites surface plasmon in the interface 10b between the metal film 12 and a material in contact with the metal film 12 and the intensity I of the component reflected in total internal reflection at the interface 10b sharply drops. That is, the particular angle of incidence is the attenuation angle θsp and the intensity I of the reflected laser beam 13 is minimized at the attenuation angle θsp. The sharp drop of the reflected laser beam 13 is observed as a dark line as indicated at D in FIG. 8.

Processing of signals output from the photodetector means 17 which represents the intensity distribution in the reflected laser beam 13 will be described in detail, hereinbelow.

Figure 10:
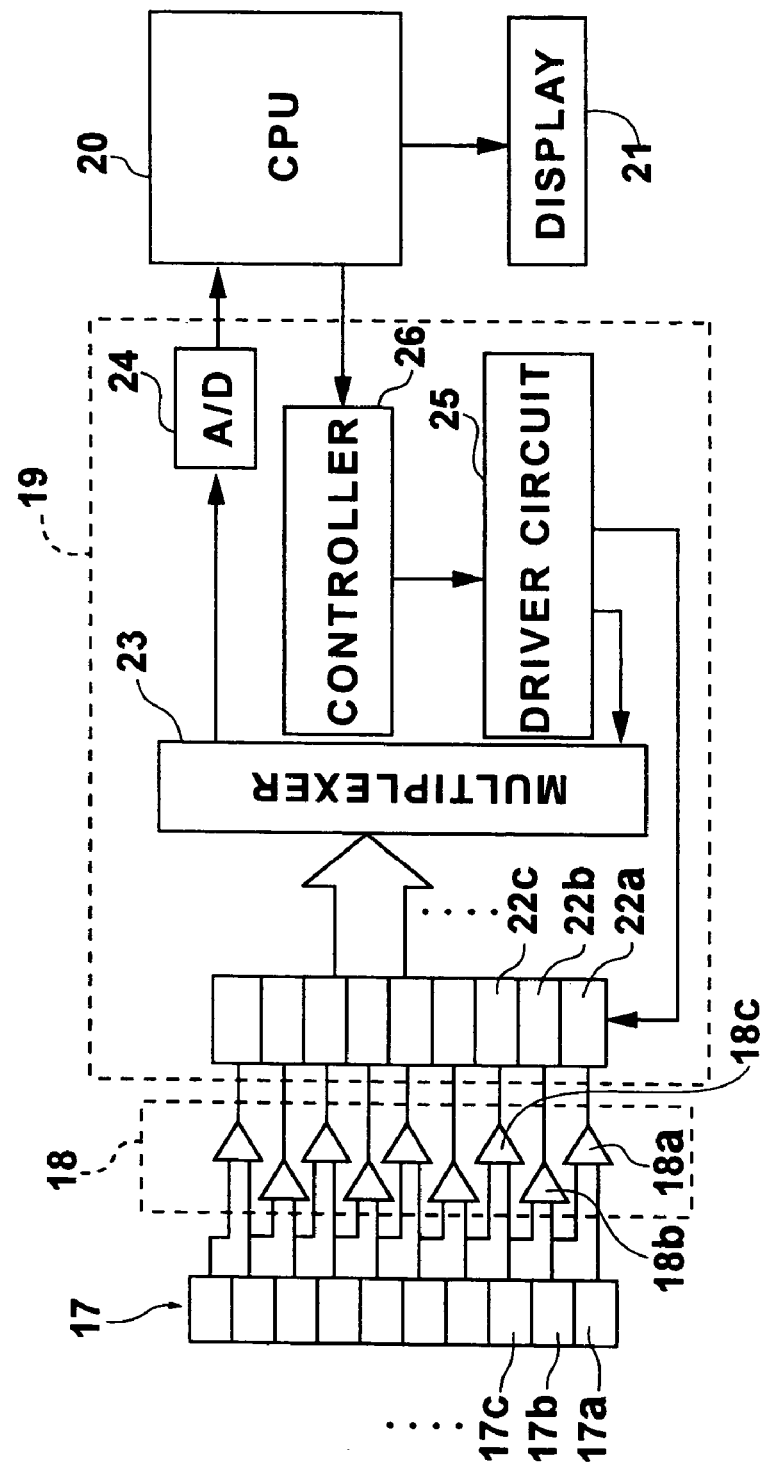
FIG. 10 is a block diagram showing the electrical arrangement of the surface plasmon resonance sensor of the third embodiment.

FIG. 10 is a block diagram showing the electrical arrangement of the surface plasmon resonance sensor of this embodiment. As shown in FIG. 10, the driver 19 comprises sample hold circuits 22a, 22b, 22c . . . which sample-hold the outputs of the respective differential amplifiers 18a, 18b, 18c . . . of the differential amplifier array 18, a multiplexer 23 into which the outputs of the sample hold circuits 22a, 22b, 22c . . . are input, an A/D convertor 24 which digitizes the outputs of the multiplexer 23 and inputs them into the signal processing section 20, a drive circuit 25 which drives the multiplexer 23 and the sample hold circuits 22a, 22b, 22c . . . , and a controller 26 which controls the drive circuit 25 under the control of the signal processing section 20.

The outputs of adjacent pairs of the photodiodes 17a, 17b, 17c . . . are respectively input into the differential amplifiers 18a, 18b, 18c . . . of the differential amplifier array 18. Accordingly, the outputs of the differential amplifiers 18a, 18b, 18c . . . of the differential amplifier array 18 represent differentials of the outputs of the photodiodes 17a, 17b, 17c . . . (representing the intensities of light which they detect) in the direction in which the photodiodes 17a, 17b, 17c . . . are arranged.

The outputs of the differential amplifiers 18a, 18b, 18c . . . are sample-held at predetermined timings by the respective sample hold circuits 22a, 22b, 22c . . . and input into the multiplexer 23. The multiplexer 23 inputs the outputs of the respective sample hold circuits 22a, 22b, 22c . . . into the A/D convertor 24 in a predetermined order. The A/D convertor 24 digitizes the outputs of the respective sample hold circuits 22a, 22b, 22c . . . and inputs them into the signal processing section 20.

Figure 11A:
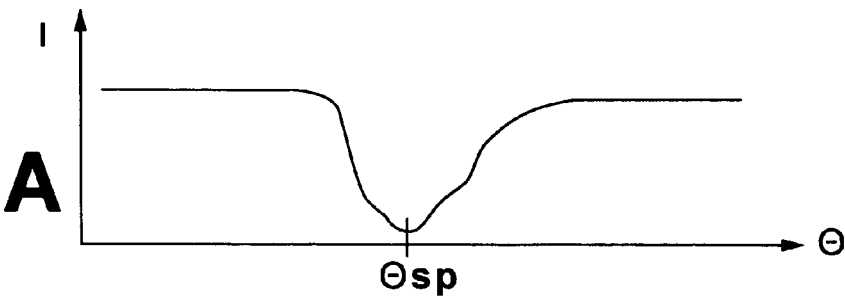
FIG. 11A is a view showing an example of the relation between the intensity I of the component of the laser beam reflected in total internal reflection at the interface and the angle of incidence θ of the component.

FIG. 11A shows an example of the relation between the intensity I of the component of the laser beam 13 reflected in total internal reflection at the interface 10b and the angle of incidence θ of the component.

Figure 11B:
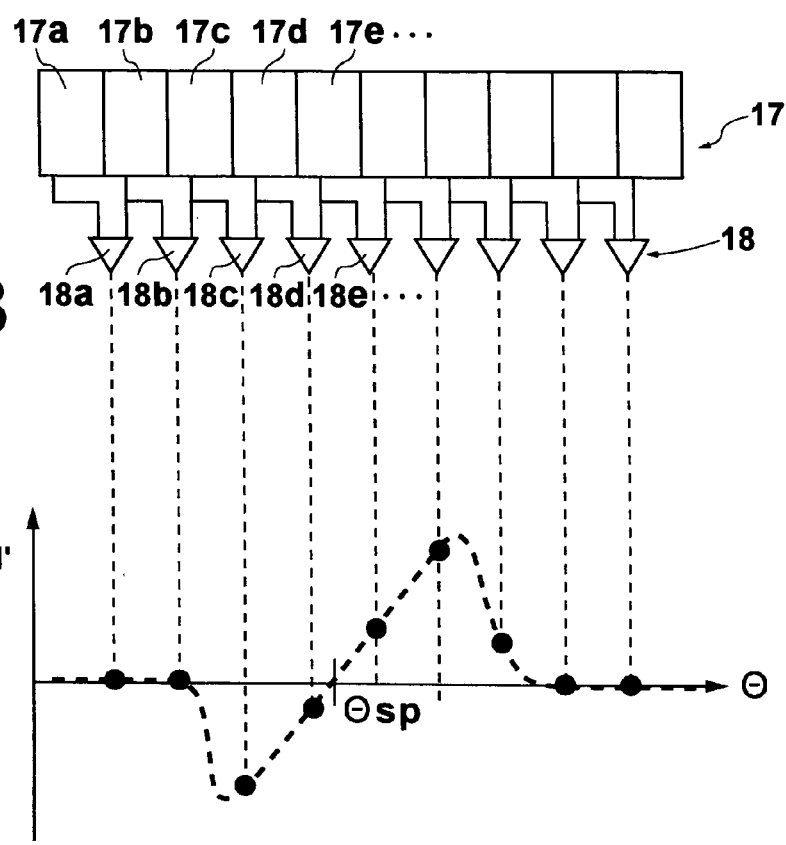
FIG. 11B is a view showing the relation between the output I' of the differential amplifier and the angle of incidence θsp.

As shown in FIG. 11B, the positions of the photodiodes 17a, 17b, 17c . . . in the direction in which they are arranged are one-to-one correspondence with the angle of incidence θsp. FIG. 11B also shows the relation between the output I' of the differential amplifier (the differential of the intensities I of the reflected laser beam 13) and the position of the photodiode 17a, 17b, 17c . . . in the direction in which the photodiodes are arranged (or the angle of incidence θsp).

The signal processing section 20 selects one of the differential amplifiers 18a, 18b, 18c . . . whose output I' is positive and the closest to 0 corresponding to the attenuation angle θsp (the differential amplifier 18e in the particular example shown in FIG. 11B) and one of the differential amplifiers 18a, 18b, 18c . . . whose output I' is negative and the closest to 0 corresponding to the attenuation angle θsp (the differential amplifier 18d in the particular example shown in FIG. 11B) on the basis of the differentials I' input into the A/D convertor 24. Then the signal processing section 20 calculates the attenuation angle θsp on the basis of the differentials output from the differential amplifiers. Sometimes there is a differential amplifier whose output I' is just 0. Naturally, the differential amplifier is selected in this case. Each time a predetermined time lapses, the signal processing section 20 repeatedly calculates the attenuation angle θsp and causes the display 21 to display the amount of change of the attenuation angle θsp from the initiation of the measurement.

Since the attenuation angle θsp changes with change of the dielectric constant or the refractive index of the material in contact with the metal film 12 of the measuring chip, change with time of the refractive index of the material in contact with the metal film 12 can be detected by detecting change of the attenuation angle θsp.

When a sensing medium 30 which combines with a particular material in the sample liquid 11 is fixed on the metal film 12, the refractive index of the sensing medium 30 changes depending on the state of combination of the sensing medium 30 and the particular material, change of the state of combination of the sensing medium 30 and the particular material can be detected by keeping measuring the differential value I'. In this case, both the sample liquid 11 and the sensing medium 30 are the object of analysis. As combinations of such a specific material and a sensing material, for instance, combinations of an antigen and an antibody have been known.

However, strictly speaking, the change of the attenuation angle θsp does not accurately reflect change of refractive index of the material in contact with the metal film 12 but can include errors due to difference in sensitivity among measuring apparatuses.

Figure 12:
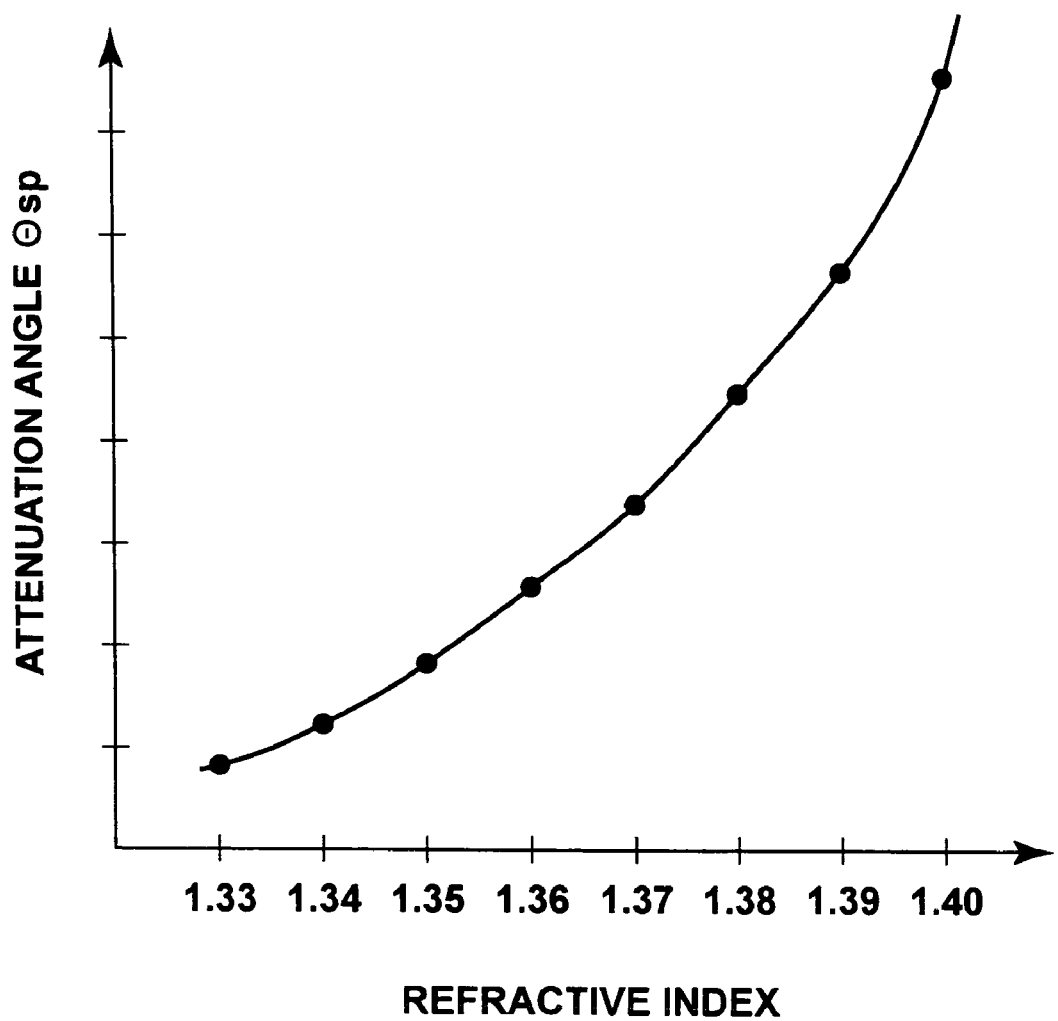
FIG. 12 is a view showing an example of calibration curve.

In order to overcome this problem, in the surface plasmon resonance sensor of this embodiment, the attenuation angle θsp of a plurality of reference sample liquids whose refractive indexes are known are measured, thereby obtaining a calibration curve such as shown in FIG. 12 on the basis of result of measurement on the reference sample liquids, and the calibration curve is stored in the built-in memory of the signal processing section 20.

Such a plurality of sample liquids can be efficiently and accurately prepared by the use of a reference sample generating means which automatically mixes two sample liquids, whose refractive indexes, in different proportions to generate a plurality of reference sample liquids of different refractive indexes.

For example, sample liquids whose refractive indexes are 1.33. to 1.40 and differ from each other by 0.01 may be employed. These reference sample liquids can be prepared by mixing distilled water whose refractive index is 1.33 and a standard refraction solution whose refractive index is 1.40 in different proportions by the use of a reference sample generating means.

Figure 15:
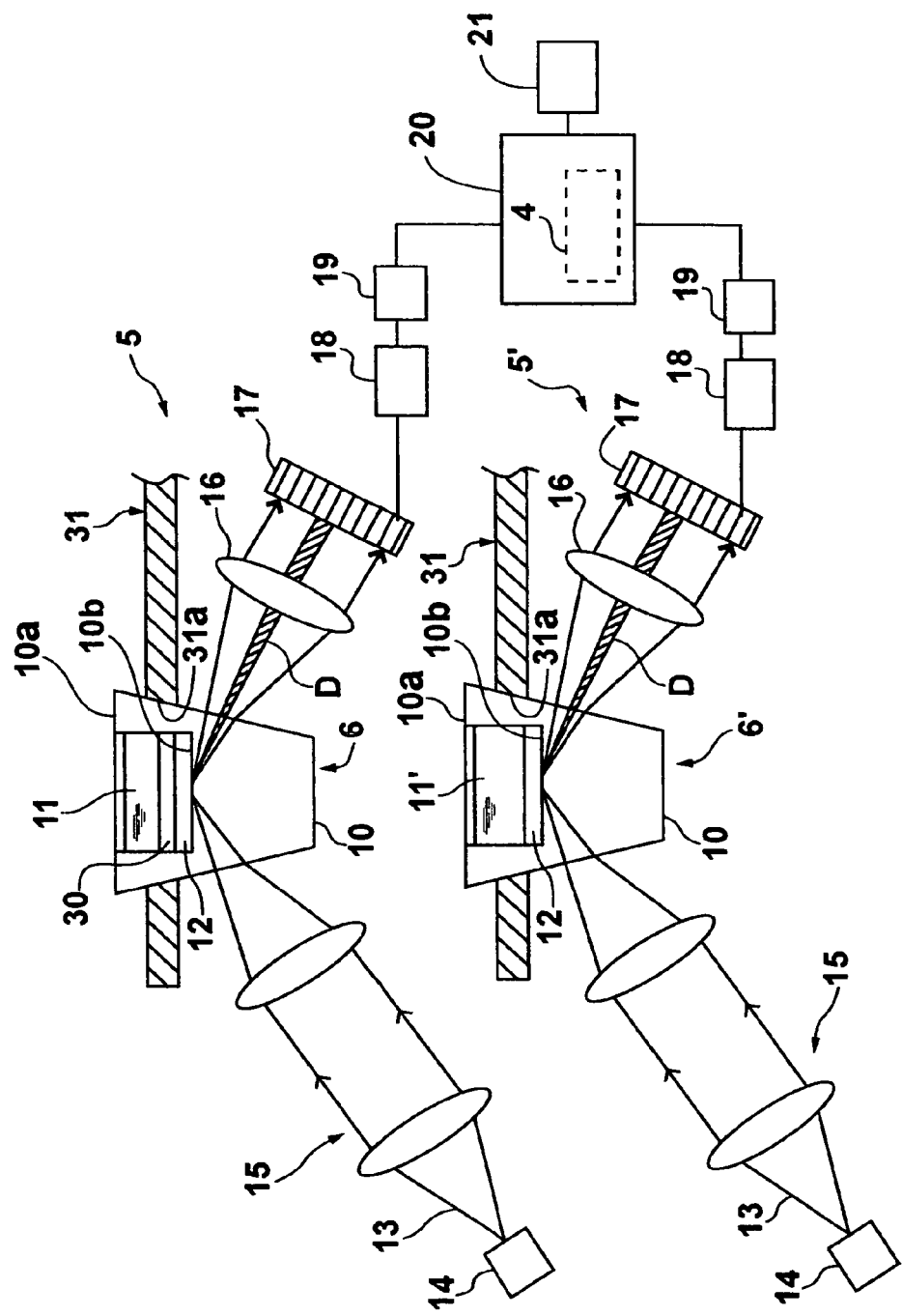
FIG. 15 is a side view of an alternative embodiment of the invention.
Figure 16:
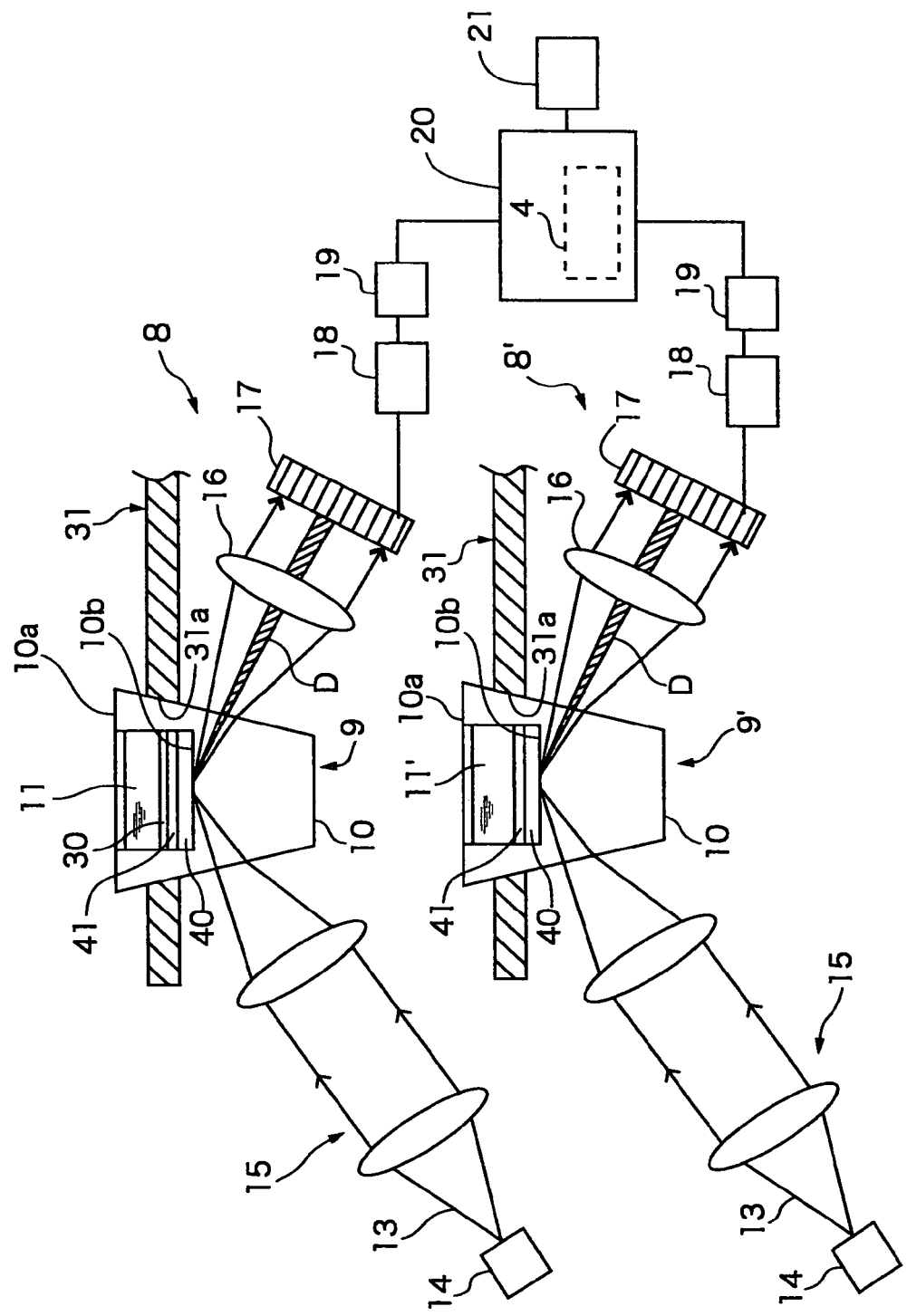
FIG. 16 is a side view of a further embodiment of the invention.

When measuring reference sample liquids, the reference sample liquids are directly spotted on metal film 12 without fixing a sensing medium on the metal film 12. FIGS. 15 and 16 illustrate embodiments of the direct spotting without a sensing medium. The remaining reference numerals correspond to elements previously described.

By calibrating result of measurement on a sample liquid 11 (and a sensing medium 30) on the basis of the calibration curve thus obtained, the difference in sensitivity among measuring apparatuses can be suppressed and the refractive index of the material in contact with the metal film 12 can be measured more accurately.

Figure 13:
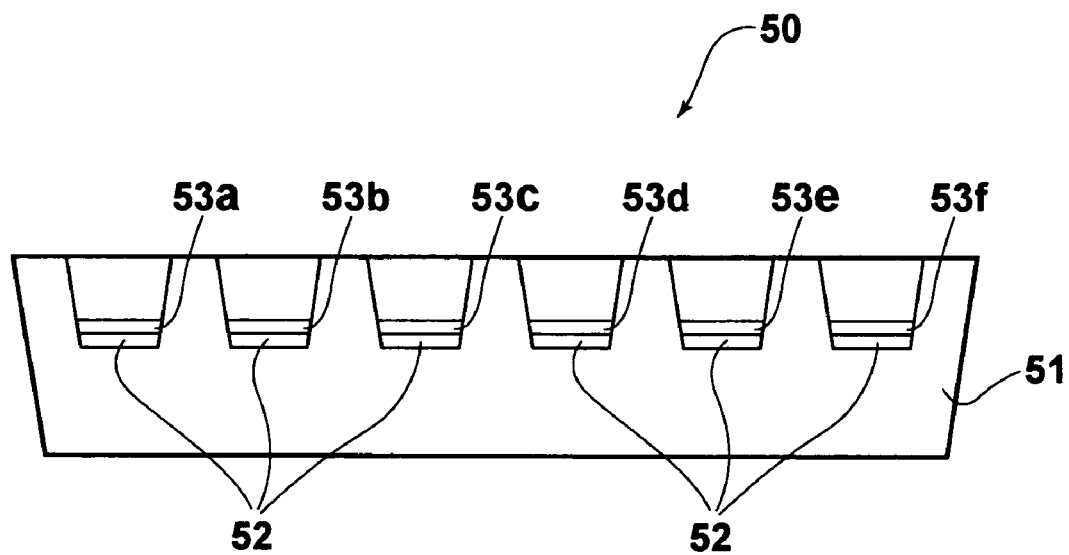
FIG. 13 is a view showing modification of the measuring chip.

The calibration curve may be obtained by the use of a measuring chip unit (a calibration jig) 50 such as shown in FIG. 13. The measuring chip unit 50 is formed integrally with dielectric blocks of a plurality of adjacent surface plasmon resonance sensor units and comprises solid materials 53a, 53b, 53c . . . (whose refractive indexes are known and different from each other) fixed on a plurality of metal films 52.

When an initial value of the differential to be measured is first obtained and the initial value is subtracted from the differential output from the differential amplifier each time the differential is measured, the remainder is free from dispersion of the absolute value according to the relation between the positions of the photodiode and the dark line and solely reflects change of the differential with time. The remainder is smaller in absolute value as compared with usual differentials and can be amplified at a sufficient amplification factor, which permits to measure change with time of the differential at high sensitivity and high accuracy.

The surface plasmon resonance sensor of this embodiment can be modified to a leaky mode sensor by changing a part thereof.

Figure 14:
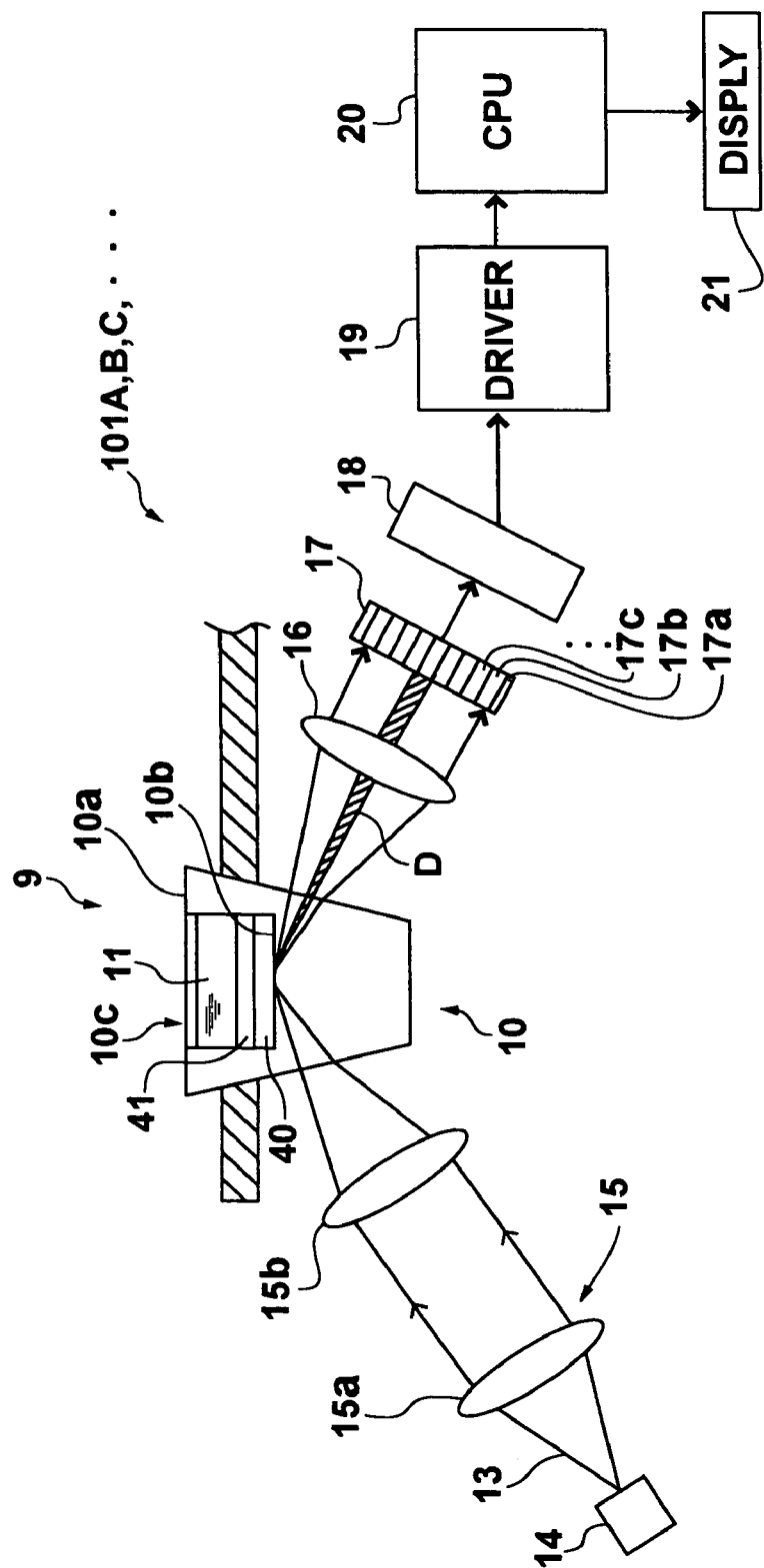
FIG. 14 is a side view of a leaky mode sensor in accordance with a fourth embodiment of the present invention.

FIG. 14 shows a leaky mode sensor in accordance with a fourth embodiment of the present invention. In FIG. 14, elements analogous to those shown in FIG. 8 are given the same reference numerals and will not be described here unless otherwise necessary.

The measuring apparatus of the fourth embodiment is substantially the same as that of the third embodiment except that the former is a leaky mode sensor and the latter is a surface plasmon resonance sensor. That is, in the leaky mode sensor of the fourth embodiment, a measuring chip 9 is employed as in the surface plasmon resonance sensor of the third embodiment.

The dielectric block 10 of the measuring chip 9 is formed of synthetic resin or optical glass (e.g., BK7), and a clad layer 40 is formed on one face of the dielectric block 10 and an optical waveguide layer 41 is formed on the clad layer 40. The clad layer 40 is in the form of film of dielectric material or metal (e.g., gold) which is lower in refractive index than the dielectric block 10. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the laser beam 13 emitted from the laser 14 is caused to impinge upon the clad layer 40 through the dielectric block 10 at an angle not smaller than an angle of total internal reflection, only light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface of the dielectric block 10 and the clad layer 40 sharply drops. That is, attenuation in total internal reflection occurs.

Since the wave number of light to be propagated through the optical waveguide layer 41 in a waveguide mode depends upon the refractive index of the sample liquid 11 on the optical waveguide layer 41, the refractive index and/or the properties of the sample liquid 11 related to the refractive index can be detected on the basis of the angle of incidence at which the attenuation in total internal reflection occurs.

What is claimed is:

1. A measuring method for detecting a state of attenuation in total internal reflection by the use of a measuring apparatus comprising a measuring unit comprising a first light source emitting a first light beam; a measuring chip comprising a first dielectric block transparent to the first light beam, a first film layer formed on one face of the first dielectric block and a first sample liquid holding system which holds a first liquid on the surface of the first film layer; a sensing material which can be combined with a specific material in the first liquid and is disposed on the first film layer; a first optical system which causes the first light beam to enter the first dielectric block to impinge upon the interface of the first dielectric block and the first film layer at various angles of incidence so that total internal reflection conditions are satisfied at the interface; and a first photodetector means which detects the intensity of the first light beam reflected in total internal reflection at the interface of the first dielectric block and the first film layer, a reference unit comprising a second light source emitting a second light beam; a reference chip comprising a second dielectric block transparent to the second light beam, a second film layer formed on one face of the second dielectric block and a second sample liquid holding system which holds a second liquid on the surface of the second film layer, a second optical system which causes the second light beam to enter the second dielectric block to impinge upon the interface of the second dielectric block and the first film layer at various angles of incidence so that total internal reflection conditions are satisfied at the interface; and a second photodetector means which detects the intensity of the second light beam reflected in total internal reflection at the interface of the second dielectric block and the second film layer, and a measuring means which corrects result of detection by the first photodetector means on the basis of result of detection by the second photodetector means and measures the change of a state of attenuation in total internal reflection on the basis of the corrected result of detection by the first photodetector means, wherein the measuring method comprises detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

2. A measuring method as defined in claim 1 in which the difference in sensitivity between the measuring unit and the reference unit is detected by causing the first and second light beams to impinge upon the interfaces at various angles of incidence so that total internal reflection conditions are satisfied at the interfaces with the first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

3. A measuring method for detecting a state of attenuation in total internal reflection by the use of a measuring apparatus comprising a measuring unit comprising a first light source emitting a first light beam; a measuring chip comprising a first dielectric block transparent to the first light beam, a first metal film formed on one face of the first dielectric block and a first sample liquid holding system which holds a first liquid on the surface of the first metal film; a sensing material which can be combined with a specific material in the first liquid and is disposed on the first metal film; a first optical system which causes the first light beam to enter the first dielectric block to impinge upon the interface of the first dielectric block and the first metal film at various angles of incidence so that total internal reflection conditions are satisfied at the interface; and a first photodetector means which detects the intensity of the first light beam reflected in total internal reflection at the interface of the first dielectric block and the first metal film, a reference unit comprising a second light source emitting a second light beam; a reference chip comprising a second dielectric block transparent to the second light beam, a second metal film formed on one face of the second dielectric block and a second sample liquid holding system which holds a second liquid on the surface of the second metal film, a second optical system which causes the second light beam to enter the second dielectric block to impinge upon the interface of the second dielectric block and the first metal film at various angles of incidence so that total internal reflection conditions are satisfied at the interface; and a second photodetector means which detects the intensity of the second light beam reflected in total internal reflection at the interface of the second dielectric block and the second metal film, and a measuring means which corrects result of detection by the first photodetector means on the basis of result of detection by the second photodetector means and measures the change of a state of attenuation in total internal reflection due to generation of surface plasmon resonance on the basis of the corrected result of detection by the first photodetector means, wherein the measuring method comprises detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

4. A measuring method as defined in claim 3 in which the difference in sensitivity between the measuring unit and the reference unit is detected by causing the first and second light beams to impinge upon the interfaces at various angles of incidence so that total internal reflection conditions are satisfied at the interfaces with the first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

5. A measuring method for detecting a state of attenuation in total internal reflection by the use of a measuring apparatus comprising a measuring unit comprising a first light source emitting a first light beam; a measuring chip comprising a first dielectric block transparent to the first light beam, a clad layer formed on one face of the first dielectric block, an optical waveguide layer which is formed on the clad layer and a first sample liquid holding system which holds a first liquid on the surface of the clad layer; a sensing material which can be combined with a specific material in the first liquid and is disposed on the clad layer; a first optical system which causes the first light beam to enter the first dielectric block to impinge upon the interface of the first dielectric block and the clad layer at various angles of incidence so that total internal reflection conditions are satisfied at the interface; and a first photodetector means which detects the intensity of the first light beam reflected in total internal reflection at the interface of the first dielectric block and the clad layer, a reference unit comprising a second light source emitting a second light beam; a reference chip comprising a second dielectric block transparent to the second light beam, a clad layer formed on one face of the second dielectric block, an optical waveguide layer which is formed on the clad layer, and a second sample liquid holding system which holds a second liquid on the surface of the clad layer, a second optical system which causes the second light beam to enter the second dielectric block to impinge upon the interface of the second dielectric block and the clad layer at various angles of incidence so that total internal reflection conditions are satisfied at the interface; and a second photodetector means which detects the intensity of the second light beam reflected in total internal reflection at the interface of the second dielectric block and the clad layer, and a measuring means which corrects result of detection by the first photodetector means on the basis of result of detection by the second photodetector means and measures the change of a state of attenuation in total internal reflection due to excitation of waveguide mode on the basis of the corrected result of detection by the first photodetector means, wherein the measuring method comprises detecting the difference in sensitivity between the measuring unit and the reference unit before initiating the measurement of the change of a state of attenuation in total internal reflection, and calibrating result of measurement by the measuring means on the basis of the difference in sensitivity between the measuring unit and the reference unit.

6. A measuring method as defined in claim 5 in which the difference in sensitivity between the measuring unit and the reference unit is detected by causing the first and second light beams to impinge upon the interfaces at various angles of incidence so that total internal reflection conditions are satisfied at the interfaces with the first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

7. A measuring apparatus utilizing the phenomenon of attenuation in total internal reflection comprising
a measuring unit comprising a first light source emitting a first light beam; a measuring chip comprising a first dielectric block transparent to the first light beam, a first film layer formed on one face of the first dielectric block and a first sample liquid holding system which holds a first liquid on the surface of the first film layer; a sensing material which can be combined with a specific material in the first liquid and is disposed on the first film layer; a first optical system which causes the first light beam to enter the first dielectric block to impinge upon the interface of the first dielectric block and the first film layer at various angles of incidence so that total internal reflection conditions are satisfied at the interface; and a first photodetector means which detects the intensity of the first light beam reflected in total internal reflection at the interface of the first dielectric block and the first film layer,
a reference unit comprising a second light source emitting a second light beam; a reference chip comprising a second dielectric block transparent to the second light beam, a second film layer formed on one face of the second dielectric block and a second sample liquid holding system which holds a second liquid on the surface of the second film layer, a second optical system which causes the second light beam to enter the second dielectric block to impinge upon the interface of the second dielectric block and the first film layer at various angles of incidence so that total internal reflection conditions are satisfied at the interface; and a second photodetector means which detects the intensity of the second light beam reflected in total internal reflection at the interface of the second dielectric block and the second film layer, and a measuring means which corrects result of detection by the first photodetector means on the basis of result of detection by the second photodetector means and measures the change of a state of attenuation in total internal reflection on the basis of the corrected result of detection by the first photodetector means,
wherein the measuring apparatus comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

8. A measuring apparatus as defined in claim 7 in which the sensitivity difference detecting means detects the difference in sensitivity between the measuring unit and the reference unit by causing the first and second light beams to impinge upon the interfaces at various angles of incidence so that total internal reflection conditions are satisfied at the interfaces with first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

9. A measuring apparatus utilizing the phenomenon of attenuation in total internal reflection comprising
a measuring unit comprising a first light source emitting a first light beam; a measuring chip comprising a first dielectric block transparent to the first light beam, a first metal film formed on one face of the first dielectric block and a first sample liquid holding system which holds a first liquid on the surface of the first metal film; a sensing material which can be combined with a specific material in the first liquid and is disposed on the first metal film; a first optical system which causes the first light beam to enter the first dielectric block to impinge upon the interface of the first dielectric block and the first metal film at various angles of incidence so that total internal reflection conditions are satisfied at the interface; and a first photodetector means which detects the intensity of the first light beam reflected in total internal reflection at the interface of the first dielectric block and the first metal film,
a reference unit comprising a second light source emitting a second light beam; a reference chip comprising a second dielectric block transparent to the second light beam, a second metal film formed on one face of the second dielectric block and a second sample liquid holding system which holds a second liquid on the surface of the second metal film, a second optical system which causes the second light beam to enter the second dielectric block to impinge upon the interface of the second dielectric block and the first metal film at various angles of incidence so that total internal reflection conditions are satisfied at the interface; and a second photodetector means which detects the intensity of the second light beam reflected in total internal reflection at the interface of the second dielectric block and the second metal film, and
a measuring means which corrects result of detection by the first photodetector means on the basis of result of detection by the second photodetector means and measures the change of a state of attenuation in total internal reflection due to generation of surface plasmon resonance on the basis of the corrected result of detection by the first photodetector means,
wherein the measuring apparatus comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

10. A measuring apparatus as defined in claim 9 in which the sensitivity difference detecting means detects the difference in sensitivity between the measuring unit and the reference unit by causing the first and second light beams to impinge upon the interfaces at various angles of incidence so that total internal reflection conditions are satisfied at the interfaces with the first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

11. A measuring apparatus utilizing the phenomenon of attenuation in total internal reflection comprising a measuring unit comprising a first light source emitting a first light beam; a measuring chip comprising a first dielectric block transparent to the first light beam, a clad layer formed on one face of the first dielectric block, an optical waveguide layer which is formed on the clad layer and a first sample liquid holding system which holds a first liquid on the surface of the clad layer; a sensing material which can be combined with a specific material in the first liquid and is disposed on the clad layer; a first optical system which causes the first light beam to enter the first dielectric block to impinge upon the interface of the first dielectric block and the clad layer at various angles of incidence so that total internal reflection conditions are satisfied at the interface; and a first photodetector means which detects the intensity of the first light beam reflected in total internal reflection at the interface of the first dielectric block and the clad layer, a reference unit comprising a second light source emitting a second light beam; a reference chip comprising a second dielectric block transparent to the second light beam, a clad layer formed on one face of the second dielectric block, an optical waveguide layer which is formed on the clad layer and a second sample liquid holding system which holds a second liquid on the surface of the clad layer, a second optical system which causes the second light beam to enter the second dielectric block to impinge upon the interface of the second dielectric block and the clad layer at various angles of incidence so that total internal reflection conditions are satisfied at the interface; and a second photodetector means which detects the intensity of the second light beam reflected in total internal reflection at the interface of the second dielectric block and the clad layer, and a measuring means which corrects result of detection by the first photodetector means on the basis of result of detection by the second photodetector means and measures the change of a state of attenuation in total internal reflection due to excitation of waveguide mode on the basis of the corrected result of detection by the first photodetector means, wherein the measuring apparatus comprises that there is further provided a sensitivity difference detecting means which detects the difference in sensitivity between the measuring unit and the reference unit before initiating the measurement of the change of a state of attenuation in total internal reflection, and said measuring means calibrates result of measurement on the basis of the difference in sensitivity between the measuring unit and the reference unit.

12. A measuring apparatus as defined in claim 11 in which the sensitivity difference detecting means detects the difference in sensitivity between the measuring unit and the reference unit by causing the first and second light beams to impinge upon the interfaces at various angles of incidence so that total internal reflection conditions are satisfied at the interfaces with the first and second liquids held by the sample holding liquid systems of the respective units, detecting changes of the attenuation in total internal reflection on the basis of the intensities of the light beams reflected at the interfaces by the measuring unit and the reference unit and comparing results of detection by the measuring unit and the reference unit, wherein the first and second liquids are the same false sample liquid comprising a solvent.

* * * * *